(12) United States Patent  
Kiesel et al.

(10) Patent No.: US 8,921,277 B2  
(45) Date of Patent: Dec. 30, 2014

(54) MULTIPLEXED FLOW ASSAY BASED ON ABSORPTION-ENCODED MICRO BEADS

(71) Applicant: Palo Alto Research Center Incorporated, Palo Alto, CA (US)

(72) Inventors: Peter Kiesel, Palo Alto, CA (US); Joerg Martini, San Francisco, CA (US); Michael I. Recht, Mountain View, CA (US)

(73) Assignee: Palo Alto Research Center Incorporated, Palo Alto, AZ (US)

( * ) Notice: Subject to any disclaimer, the term of this patent is extended or adjusted under 35 U.S.C. 154(b) by 4 days.

(21) Appl. No.: 13/627,739

(22) Filed: Sep. 26, 2012

(65) Prior Publication Data

US 2014/0087971 A1 Mar. 27, 2014

(51) Int. Cl.
*C40B 30/10* (2006.01)
*C40B 50/14* (2006.01)
*C40B 60/12* (2006.01)

(52) U.S. Cl.
USPC .................................................. 506/7

(58) Field of Classification Search
USPC .................................................. 506/7
See application file for complete search history.

(56) References Cited

U.S. PATENT DOCUMENTS

| | | | |
|---|---|---|---|
| 4,081,277 A | 3/1978 | Brault et al. | |
| 5,682,038 A | 10/1997 | Hoffman | |
| 5,745,308 A | 4/1998 | Spangenberg | |
| 5,880,474 A | 3/1999 | Norton et al. | |
| 7,358,476 B2 | 4/2008 | Kiesel et al. | |
| 7,496,463 B2 | 2/2009 | Nicoli et al. | |
| 7,701,580 B2 | 4/2010 | Bassler et al. | |
| 7,763,856 B2 | 7/2010 | Kiesel et al. | |
| 7,817,254 B2 | 10/2010 | Hegyi et al. | |
| 7,830,517 B2 | 11/2010 | Beck et al. | |
| 7,894,068 B2 | 2/2011 | Bassler et al. | |
| 2007/0145249 A1 | 6/2007 | Kiesel et al. | |
| 2008/0181827 A1 | 7/2008 | Bassler et al. | |
| 2008/0183418 A1 | 7/2008 | Bassler et al. | |
| 2009/0195773 A1 | 8/2009 | Bassler et al. | |
| 2009/0195852 A1 | 8/2009 | Bassler et al. | |
| 2010/0155572 A1 | 6/2010 | Kiesel et al. | |
| 2010/0155577 A1 | 6/2010 | Kiesel et al. | |
| 2010/0157291 A1 | 6/2010 | Kiesel et al. | |
| 2010/0201988 A1 | 8/2010 | Kiesel et al. | |
| 2010/0222289 A1* | 9/2010 | Lerner | 514/29 |

(Continued)

FOREIGN PATENT DOCUMENTS

CA 2767032 A1 * 2/2005

OTHER PUBLICATIONS

Kim et al., Alalytical Bioanalytical Chemistry, 2010, 398, pp. 2373-2382.*

(Continued)

*Primary Examiner* — Larry Riggs
*Assistant Examiner* — Karla Dines
(74) *Attorney, Agent, or Firm* — Hollingsworth Davis, LLC

(57) ABSTRACT

Analysis of a system and/or sample involves the use of absorption-encoded micro beads. Each type of micro bead is encoded with amounts of the k dyes in a proportional relationship that is different from proportional relationships of the k dyes of others of the n types of absorption-encoded micro beads. A system and/or a sample can be analyzed using information obtained from detecting the one or more types of absorption-encoded micro beads.

19 Claims, 24 Drawing Sheets

(56) References Cited

U.S. PATENT DOCUMENTS

| | | | |
|---|---|---|---|
| 2011/0222062 A1 | 9/2011 | Martini et al. | |
| 2011/0263457 A1* | 10/2011 | Krutzik et al. | 506/15 |
| 2012/0088307 A1* | 4/2012 | Singh et al. | 436/86 |

OTHER PUBLICATIONS

Kraan et al., Journal of Biological Regulators and Homeostatic Agents, 2003, 17, pp. 223-233.*

Telford et al., Cytometry, May 2009, 75(5), pp. 450-459.*

Jun et al., Molecules, 2012, pp. 2474-2490.*

Kiesel et al., "'Spatially modulated emission' advances point-of-care diagnostics", Laser Focus World, Nov. 2010, pp. 47-50.

Engvall et al., "Enzyme-linked immunosorbent assay (ELISA). Quantitative assay of immunoglobulin G", Immunochemistry. 8(9), 871-874 (1971).

Van Weemen et al., "Immunoassay using antigen enzyme conjugates", FEBS Lett. 15(3), 232-236 (1971).

U.S. Appl. No. 13/206,436, filed Aug. 9, 2011, Kiesel et al.

U.S. Appl. No. 13/206,439, filed Aug. 9, 2011, Kiesel et al.

Schena et al., "Quantitative monitoring of gene expression patterns with a complementary DNA microarray", Science, 270(5235), 467-470 (1995).

Kulesh et al., "Identification of interferon-modulated proliferation-related cDNA sequences", Proc Natl Acad Sci USA. 84(23), 8453-8457 (1987).

Linman et al., "Interface design and multiplexed analysis with surface plasmon resonance (SPR) spectroscopy and SPR imaging", Analyst. 135(11), 2759-2767 (2010).

Nahshol et al.,"Parallel kinetic analysis and affinity determination of hundreds of monoclonal antibodies using the ProteOn XPR36", Anal Biochem. 383(1), 52-60 (2008).

Chowdhury et al., "Validation and comparison of two multiplex technologies, Luminex® and Mesoscale Discovery, for human cytokine profiling", Journal of Immunological Methods 340(1), 55-64 (2009).

"Human Cytokine/Chemokine Magnetic Bead Panel", http://www.millipore.com/userguides.nsf/a73664f9f981af8c852569b9005b4eee/e1dbeddc233bfd438525767f00679241/$FILE/HCYTOMAG-60K.MPX.pdf, (2011).

\* cited by examiner

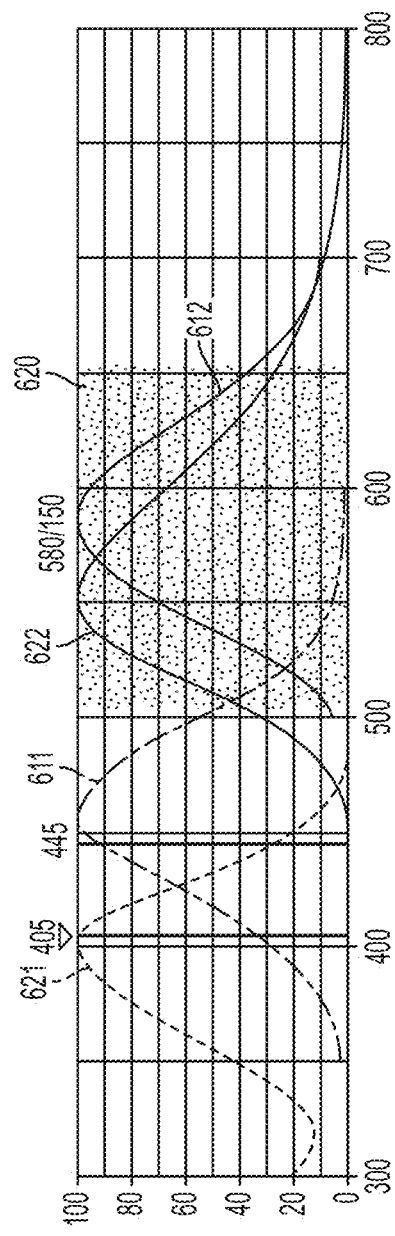
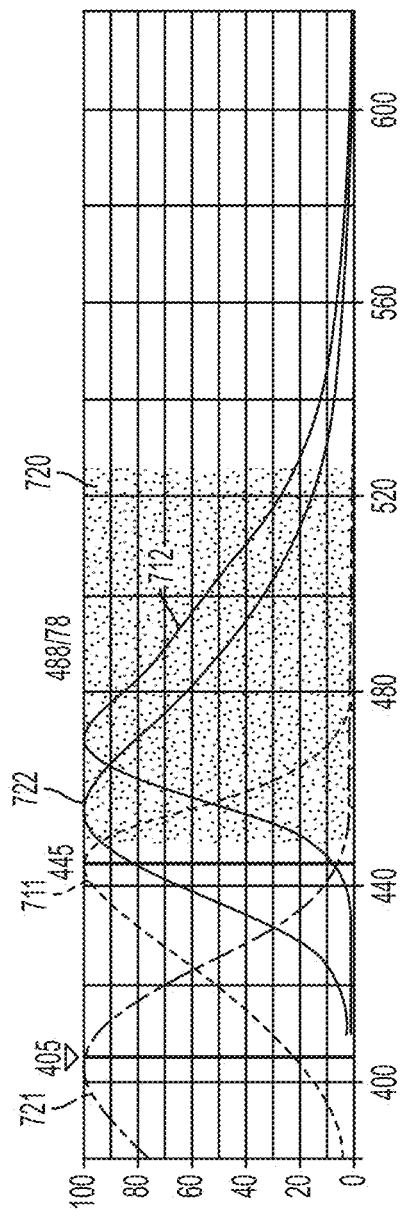
FIG. 6
FIG. 7

MULTIPLEXED FLOW ASSAY BASED ON ABSORPTION-ENCODED MICRO BEADS

STATEMENT REGARDING FEDERALLY SPONSORED RESEARCH AND DEVELOPMENT

This invention was made with government support under contract number 1R21EB011662-01, awarded by the National Institutes of Health (NIH). The U.S. Government has certain rights in this invention.

SUMMARY

Some embodiments involve a method of analyzing properties of a system. Light emission is stimulated from k dyes encoding n type of absorption-encoded micro beads present in a sample. Each k dye has an absorption spectrum that is distinguishable from absorption spectra of others of the k dyes. Stimulating the light emission comprises selectively stimulating each of the k dyes without substantially stimulating others of the k dyes. The k dyes encode n types of absorption-encoded micro beads, each type of micro bead encoded with amounts of the k dyes in a proportional relationship that is different from proportional relationships of the k dyes of others of the n types of absorption-encoded micro beads. One or more types of absorption-encoded micro beads present in the sample are detected based on light emission from the k dyes that encode the types of absorption-encoded micro beads. One or more properties of a system are analyzed using information obtained from detecting the one or more types of absorption-encoded micro beads.

Various embodiments are directed to an analyzer configured to analyze properties of system. The analyzer includes k light sources configured to selectively stimulate light emission from k dyes. Each k dye has an absorption spectrum that is distinguishable from absorption spectra of others of the k dyes. Selective stimulation the k dyes includes stimulating each k dye without substantially stimulating others of the k dyes. The k dyes encode n types of absorption-encoded micro beads, each type of absorption-encoded micro bead encoded with amounts of the k dyes in a proportional relationship that is different from proportional relationships of the k dyes of others of the n types of absorption-encoded micro beads. The analyzer includes one or more photosensitive detectors configured to sense the light emission from the k dyes and to generate an output signal. A processor is configured to analyze the output signal to detect the n types of absorption-encoded micro beads based on the light emission from the k dyes and to analyze one or more properties of the system using information obtained from one or more types of absorption-encoded micro beads present in a sample.

Some embodiments involve a method of using n types of absorption-encoded micro beads to detect target analytes in a sample. Each type of absorption-encoded micro bead is encoded with k dyes in a proportional relationship that is different from proportional relationships of the k dyes of others of the n types of absorption-encoded micro beads. Each k dye has an absorption spectrum that is distinguishable from absorption spectra of others of the k dyes, the n types of absorption-encoded micro beads being functionalized with recognition elements configured to interact with n target analytes, respectively. Excitation light that is configured to stimulate light emission from the k dyes encoding the absorption-encoded micro beads present in a sample is provided. Each of the k dyes is selectively stimulated without substantial stimulation of light emission from others of the k dyes. Excitation light configured to stimulate light emission from a label dye is stimulated, where the light emission from the label dye is indicative of a presence of one or more analytes in the sample. The method includes sensing for light emanating from the micro beads, the light emanating from each micro bead including one or more of light emission from the k dyes and light emission from the label dye. One or more types of absorption-encoded micro beads present in the sample are detected based on the light emanating from the micro beads. One or more target analytes present in the sample are detected based on the light emanating from the micro beads.

Various embodiments are directed to a system configured to detect n types of micro beads and/or to detect target analytes. The system includes k light sources configured to stimulate light emission from each of k dyes, respectively. Each k dye having an absorption spectrum that is distinguishable from absorption spectra of others of the k dyes. The distinguishable absorption spectra of the k dyes allowing selective stimulation of each k dye without substantially stimulating others of the k dyes. The k dyes encode n types of absorption-encoded micro beads, wherein each type of absorption-encoded micro bead is encoded with amounts of the k dyes in a proportional relationship that is different from proportional relationships of the k dyes of others of the n types of absorption-encoded micro beads. The n types of absorption-encoded micro beads are functionalized with n recognition elements, respectively, the n recognition elements configured to interact with n target analytes, respectively. The system also includes one or more photosensitive detectors configured to sense the light emission from the k dyes. A processor is configured to detect the n types of micro beads present in a sample based on the light emission from the k dyes and to detect the n target analytes.

A method of fabricating micro beads involves encoding n types of micro beads with k dyes, each k dye having an absorption spectrum that is distinguishable from absorption spectra of others of the k dyes. After the encoding, each type of micro bead includes the k dyes in a proportional relationship that is different from proportional relationships of the k dyes of others of the n types of micro beads. The absorption spectra of the k dyes allows selective stimulation of light emission from each of the k dyes without substantially stimulating light emission from others of the k dyes. The n types of micro beads are functionalized with n recognition elements, respectively, the n recognition elements configured to interact with n target analytes, respectively.

Related methods, systems, articles, and components are also discussed.

These and other aspects of the present application will be apparent from the detailed description below. In no event, however, should the above summaries be construed as limitations on the claimed subject matter, which subject matter is defined solely by the attached claims.

BRIEF DESCRIPTION OF THE DRAWINGS

FIGS. 5-10 are sets of graphs showing absorption and emission spectra for illustrative fluorescent dye combinations that may be used to encode micro beads in proportional relationships to indicate different micro bead types;

Like reference numbers refer to like components.

Figure 1:
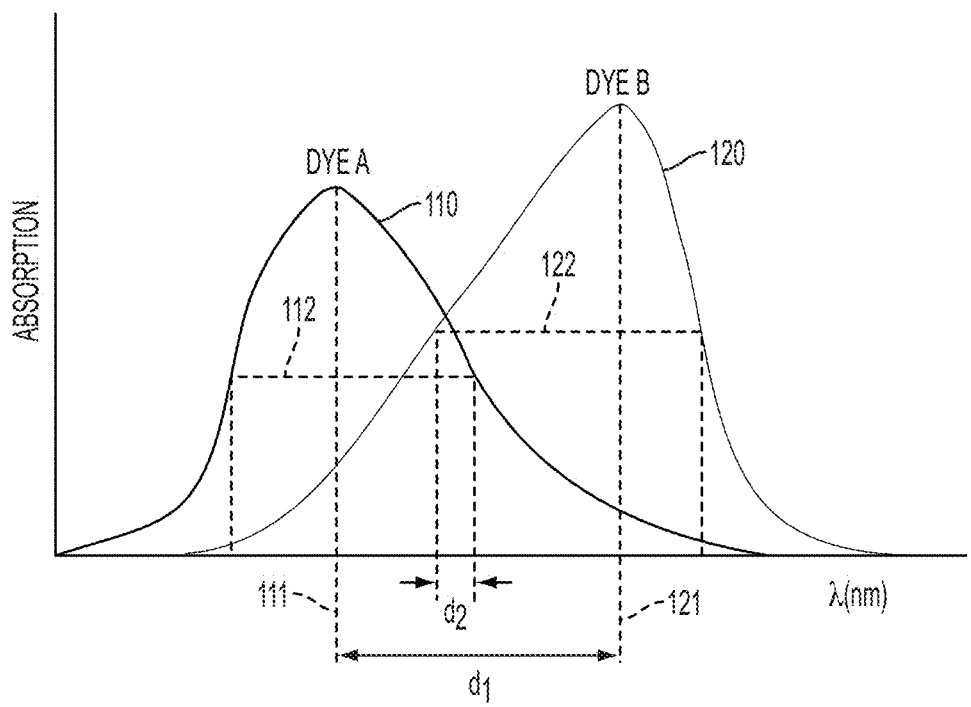
FIG. 1 illustrates absorption spectra of two dyes that are distinguishable.

Drawings are not necessarily to scale unless otherwise indicated.

DETAILED DESCRIPTION OF ILLUSTRATIVE EMBODIMENTS

Across a variety of technological areas, absorption-encoded micro beads can be designed and implemented to function as miniature, free flowing sensors. Analysis approaches described herein involve detection of absorption-encoded micro beads that have been encoded, e.g. filled, injected, coated, stained or treated, etc. with combinations of dyes having excitation spectra that are distinguishable from one another. The k dyes can be used to encode n types of micro beads such that each type of micro bead includes the k dyes in a proportional relationship that is different from the proportional relationships of the k dyes included in others of the n types of absorption-encoded micro beads. Each of the n types of micro bead may have characteristics different from other types of the micro beads, e.g., size, shape, charge, porosity, surface characteristics, elasticity, material composition and/or may each type of micro bead may be respectively functionalized to recognize particular analytes.

For example, absorption-encoded micro beads can be added to a sample that is taken from or which interacts with a system. The absorption encoded micro beads are detected by an analyzer configured to analyze properties of the system based on information obtained from the micro beads. In some cases, the system can be a biological system, such as the human body, the sample (such as a blood sample) is taken from the human body, and the micro beads are added to the sample.

As another example, the integrity of a filter can be tested using micro beads of different types in a sample that pass through or interact with the filter. Each type of micro bead is encoded with the k dyes a known proportional relationship which identifies the type micro bead. Each type of micro bead may have a particular physical characteristic, e.g., size, charge, shape, surface texture, elasticity, material composition, and so forth. The types of micro beads that have interacted with the filter are detected and one or more transmission properties of the filter can be determined based on the types of micro beads that have interacted with the filter.

As another example, in some implementations, the absorption-encoded micro beads can be functionalized with recognition elements that interact with certain analytes in a sample. During analysis of the sample, the types of micro beads present in the sample are detected based on the absorption spectra of the characteristic combination of dyes that identifies the type of micro bead. Additionally, information about the presence and/or quantity of one or more analytes in the sample can be determined based on whether and/or to what extent the analytes have interacted with the recognition elements of the micro beads.

Embodiments described herein involve the use of absorption-encoded micro beads that can be deployed in a variety of applications, including analysis of system properties and/or detection of the presence and/or amount of an analyte in a sample. In some implementations, such as advanced diagnostics, multiple analytes in a sample may need to be detected in an assay. Absorption-encoded micro beads can be used in a multiplexed assay designed to identify the presence and/or amounts of multiple analytes.

FIG. 1 illustrates the distinguishable absorption spectra 110, 120 of two dyes, labeled DYE A and DYE B. The peak absorption wavelength 111 of the DYE A is separated from the peak absorption wavelength 121 of the DYE B by $d_1$, which can be a few nm to a few hundred nm. The full width half maximum (FWHM) 112 of the first excitation spectrum 110 of DYE A and the FWHM 122 of the second excitation spectrum 120 of DYE B are shown in FIG. 1. The overlap between the FWHM 112 of the first excitation spectrum 110 and the FWHM 122 of the second excitation spectrum 120, $d_2$, is less than half of the FWHM 112, 122 of either dye. The difference in the absorption spectra should be as large as possible and sufficient to enable a clear differentiation between types of micro beads as discussed in more detail below.

The various embodiments described herein refer to micro beads used in the analysis of a sample and/or system. It will be understood that the systems and methods described herein are applicable to detect various analytes or particles present in a sample. The term "particles" or "analytes" refers broadly to any object of interest to be detected. In some applications, particles or analytes of interest are relatively small, and may be microscopic in size. A given particle or analyte may be or include one or a collection of biological cell(s), virus(es), molecule(s), certain proteins, DNA or RNA fragments, sub-molecular complex(es), droplets (e.g. oil in water), gas bubbles, or other bit(s) of matter, for example.

Figure 2:
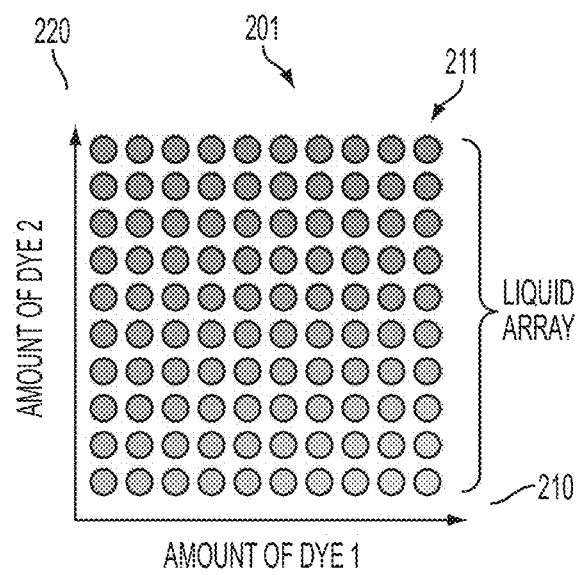
FIG. 2 shows an array of absorption-encoded micro beads.

FIG. 2 shows an array 201 of absorption-encoded micro beads 211 of various types that may be used to perform a number of analytical processes. Note that in many cases there will be many micro beads 211 of each particular micro bead type in a sample.

The micro beads 211 are treated, e.g., coated, filled, stained or tagged or otherwise associated with a combination of suitable fluorescent dyes or other agents (all of which are collectively referred to herein as "dyes") in such a way that they emit light in a predictable fashion when illuminated with excitation light. In this regard, the light emitted by a given excited dye may be fluorescent in nature, or it may constitute a form of scattered light such as in the case of Raman scattering. The reader will therefore understand that when we refer to, for example, incident light that is effective to excite a dye, such incident excitation light may be selectively absorbed by the dye so as to cause the dye to fluoresce, or such incident excitation light may selectively interact in some other way with the micro bead, e.g. so as to cause resonant Raman scattering. In any case, the emitted light is preferably shifted in wavelength to some extent relative to the excitation light so that at least a portion of the emitted light can be at least partially isolated from the excitation light with one or more suitable filters. Whatever the nature of the light emitted by a dye, such emitted light also preferably responds relatively rapidly to excitation light so that if the excitation light is modulated at a particular frequency ν, the emitted light will also fluctuate to some measurable extent at the frequency ν.

In the illustrated example, each micro bead type is encoded using combinations of two dyes, denoted in FIG. 2 as dye 1 and dye 2. Dye 1 has a first excitation (absorption) spectrum that is distinguishable from the absorption spectrum of dye 1. Dye 2 has a second excitation (absorption) spectrum that is distinguishable from the absorption spectrum of dye 1. Moving along the x-axis 210 from left to right means that the amount of dye 1 for the micro bead type is increasing. Moving along the y-axis 220 from bottom to top means that the amount of dye 2 for the micro bead type is increasing. The shading of the micro bead 211 indicates the different combinations of dye 1 and dye 2, and thus different absorption encoding of each micro bead 211 according to micro bead type. Although the micro beads 211 of different types have different absorption spectra, they do not necessarily emit light in different spectral ranges. In other words, two micro bead types that have distinguishable absorption spectra may have indistinguishable emission spectra.

In general, each type of micro bead is absorption encoded using k dyes with distinguishable absorption spectra. In many cases, only two or three dyes are used to encode the micro beads because this number of dyes can provide encoding for many micro bead types, e.g., between 20 and 1000, which is usually sufficient for a large number of assays.

Figure 3:
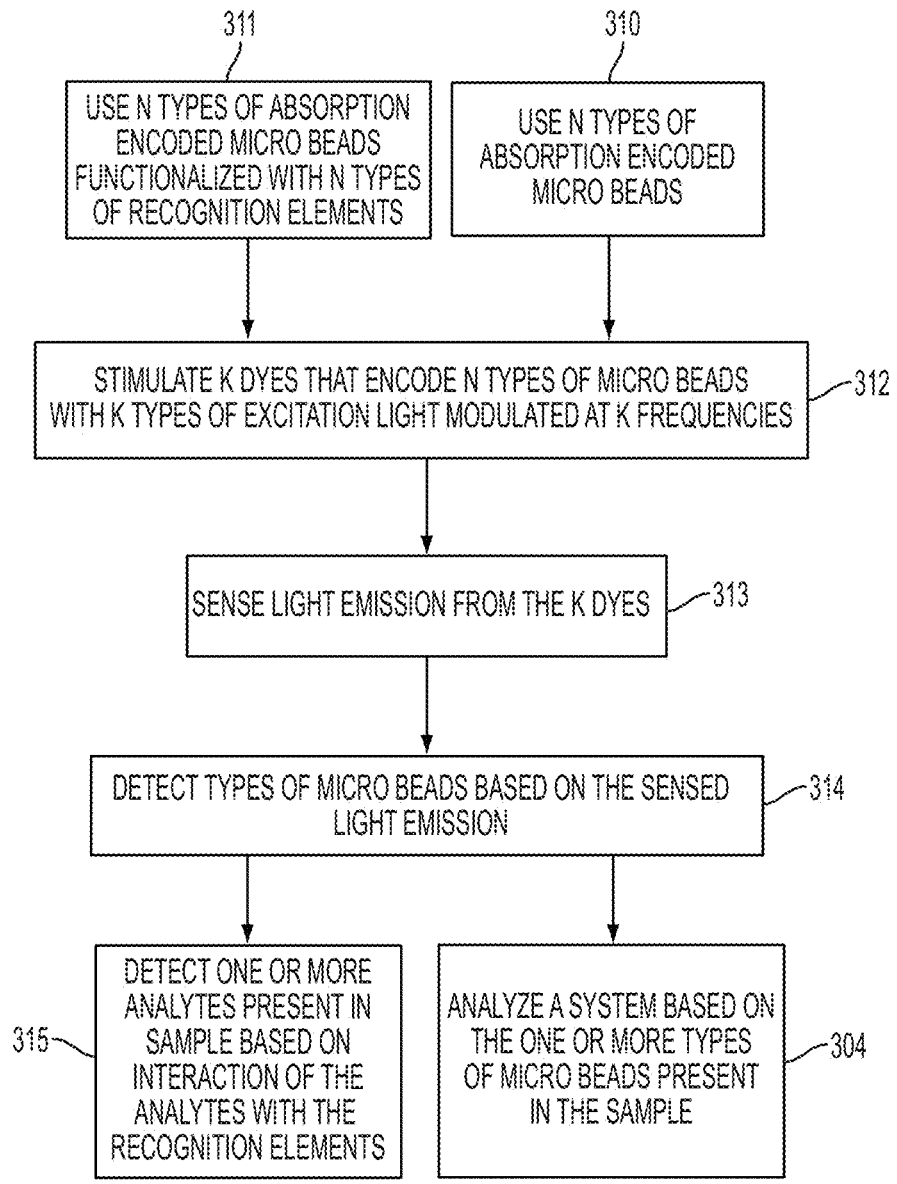
FIG. 3 is a flow diagram illustrating methods of using absorption-encoded micro beads.

The absorption-encoded micro beads can be used in a variety of ways to analyze a sample and/or to evaluate a system associated with, or interacting with, the sample. FIG. 3 is a flow diagram of processes for using micro beads to analyze a sample and/or a system. According to some implementations, a process optionally involves using 310 n types of micro beads encoded with k dyes. Excitation light is provided, wherein the excitation light is configured to stimulate 312 light emission from k dyes that encode micro beads present in a sample. The excitation light may be intensity modulated at k frequencies. Each k dye has an absorption spectrum that is distinguishable from absorption spectra of others of the k dyes. Stimulating the light emission comprises selectively stimulating each of the k dyes without substantially stimulating others of the k dyes. The k dyes encode n types of absorption-encoded micro beads, each type of micro bead is encoded with amounts of the k dyes in a proportional relationship that is different from proportional relationships of the k dyes of others of the n types of absorption-encoded micro beads.

Light emission from the k dyes that encode the micro beads is sensed 313. One or more types of absorption-encoded micro beads present in the sample are detected 314 based on light emission from the k dyes. According to one optional process, properties of a system are analyzed 304 using information obtained from detecting the one or more types of absorption-encoded micro beads present in the sample. For example, the analysis may involve counting the number of micro beads, counting the number of types of micro beads, and/or determining an amount of analyte that has interacted with the micro bead.

In some embodiments, the n types of micro beads may have a range of characteristics that can be used to analyze the system. For example, each of the micro bead types may have a different value of at least one characteristic of interest such as size, shape, surface texture, charge, material, hydrophilism, hydrophobism, elasticity, and/or porosity. For example, each micro bead type may have a different size; each micro bead type may have a different shape, or a different surface texture, etc., from other types of micro beads. In some embodiments, the absorption-encoded micro beads having various physical properties as discussed above may be used to determine the integrity of a filter.

In one specific example, the system comprises a filter and the n types of micro beads have different sizes. Evaluating the properties of the filter comprises determining which types of the micro beads (corresponding to different micro bead sizes) pass through the filter.

As also illustrated in the flow diagram of FIG. 3, in some cases, the n types of absorption-encoded micro beads are functionalized 311 with n types of recognition elements, respectively. The n types of recognition elements are configured to interact with n analytes, respectively. Light emission is stimulated 312 from the k dyes by illuminating the k dyes using k light sources emitting k types of excitation light, respectively. Each of the k types of excitation light stimulates light emission from one of the k dyes without substantially stimulating light emission from others of the k dyes. The k types of light can be modulated at k frequencies, $\nu_1$, $\nu_2$, $\nu_3$, ... $\nu_k$, respectively.

The light emission from the k dyes is sensed 313. Each type of absorption-encoded micro bead present in the sample is detected 314 based on the light emission from the k dyes. One or more target analytes in the sample are detected 315 based on interaction between the one or more target analytes with their corresponding recognition elements.

Figure 4:
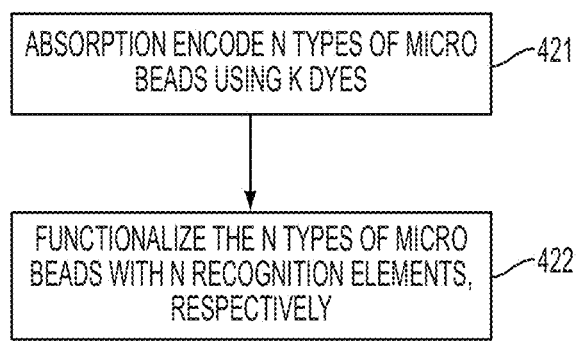
FIG. 4 is a flow diagram illustrating a method of fabricating absorption-encoded micro beads.

The flow diagram of FIG. 4 illustrates a method of fabricating absorption-encoded micro beads. N types of micro beads are absorption-encoded 421 with k dyes. Each k dye has an absorption spectrum that is distinguishable from the absorption spectra of others of the k dyes. After the encoding, each type of micro bead includes the k dyes in a proportional relationship that is different from proportional relationships of the k dyes of others of the n types of micro beads. The absorption spectra of the k dyes allows selective stimulation of light emission from each of the k dyes without substantially stimulating light emission from others of the k dyes. Optionally, the n types of micro beads can in addition be functionalized 422 with n recognition elements, respectively. The n recognition elements configured to interact with n target analytes, respectively. The n recognition elements can be associated with one or more label dyes.

Figure 5:
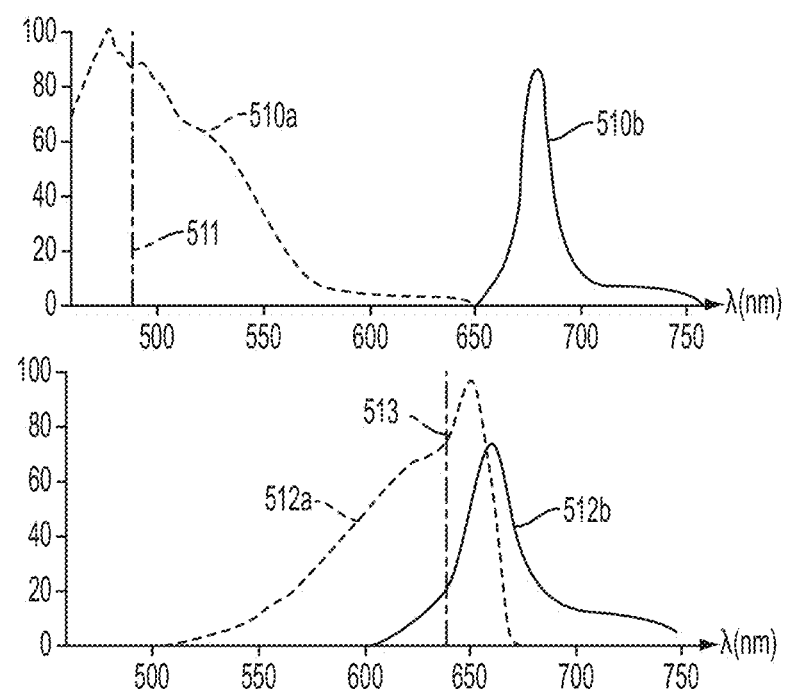

For example, for k=2, one useful dye combination to achieve absorption encoding is Peridinin Chlorophyll Protein (PerCP) complex and Allophycocyanin (APC) dye. FIG. 5 is a set of graphs showing the absorption spectra and emission spectra for Peridinin Chlorophyll Protein (PerCP) complex and Allophycocyanin (APC) dye. In the upper graph, curve 510*a* represents the absorption spectrum for PerCP complex. Curve 510*b* represents the emission spectrum for PerCP. In the lower graph, curve 512*a* represents the excitation spectrum for APC dye. Curve 512*b* represents the emission spectrum for APC. One can readily see, based on the significant differences between curves 510*a* and 512*a*, that the absorption characteristics of PerCP and APC are distinguishable from each other so that excitation light of different wavelengths can be used to selectively excite PerCP and APC for all proportional relationships of the two dyes. PerCP and APC have almost complementary excitation spectra but similar emission spectra, and this dye combination allows for a simple implementation in which the different types of micro beads can be distinguished.

Depending on the application, the available excitation sources, and the emission filter(s) used, a larger variety of dye combinations can be selected. For example, available Internet tools such as the interactive spectrum viewer provided by BD Biosciences, or the interactive spectrum viewer provided by Life Technologies Corporation can be used for dye selection. A criterion is that the dye excitation characteristics (e.g., absorption spectra) are different enough so that a first excitation source emitting a first spectrum that significantly overlaps with the excitation spectrum of the first dye but does not significantly overlap with the excitation spectrum of the second dye can be used to produce a larger detector signal for the first dye, and a second excitation source emitting a second excitation spectrum that significantly overlaps with the excitation spectrum of the second dye but does not significantly overlap with the excitation spectrum of the first dye can be used to produce a larger detector signal for the second dye. From the light emission from the first dye and the second dye, the proportional relationship of the k dyes that encodes a micro bead type can be determined, that from the proportional relationship, the micro bead type can be identified.

The spectral characteristics provided in FIG. 5 show that two light sources emitting two different spectra can be used to independently excite micro beads of the first type (e.g., encoded with PerCP and APC in the proportional relationship 100% PerCP and 0% APC) and micro beads of the second type (e.g., encoded with PerCP and APC in the proportional relationship 0% PerCP and 100% APC). Note that although proportional relationships of 100% PerCP/0% APC and 100% APC/0% PerCP are used in this illustrative example, it will be appreciated that other proportional relationships could be used.

In some configurations, a first laser source operating at $\lambda_{Ex1}$=488 nm (see line 511 in FIG. 5) and a second laser source operating at $\lambda_{Ex2}$=638 nm (see line 513 in FIG. 5) may be selected for the two light sources used to excite the dyes. Curves 510*b*, 512*b* in FIG. 5 reveal that the fluorescent light emitted by the first and second types of micro beads can be readily detected by a single detector, e.g., a silicon photodiode or avalanche photodiode, possibly equipped with a suitable optical filter. The filter may for example be a high pass filter transmitting in a wavelength range above 650 nm, or above 660 nm, or the filter may be a band pass filter transmitting in a wavelength range from about 665 nm to 705 nm, for example. Band pass filters having suitable pass bands for the PerCP/APC dye combination are 685/40 nm or 725/150 nm (available for example from Semrock, Inc.). The use of a high pass or band pass filter allows detection of the light emission from the dyes while blocking or substantially attenuating the excitation light emitted by the light sources to excite the dyes.

There are a number of combinations of fluorescence dyes that exhibit different absorption spectra but have similar emission spectra, including the PerCP/APC combination discussed above. Many of these dye combinations have absorption spectra, which are distinguishable and allow selective excitation of the dyes in the various proportional relationships that can be used to identify the types of micro beads. Furthermore, in many cases, the same filter/detector combination can be used to detect the light emission from the dyes because the emission spectra of the dyes substantially overlap. Especially interesting are combinations that can be excited with currently available laser diodes or light emitting diodes (LEDs) (e.g., resonant cavity (RC-LEDs) and high power LEDs). Low cost and high performance light sources of this kind are currently available, for example, with emission wavelengths around 375 nm, 405 nm, 445 nm, 510 nm, 635 nm, 650 nm, and 670 nm. FIGS. 6 and 7 show two different dye combinations, 4-(4-(Dihexadecylamino)styryl)-N-Methylpyridinium Iodide (DiA) and Pacific Orange (FIG. 6) and SYTOX Blue and Pacific Blue (FIG. 7) which can be used to encode types of micro beads using different proportional relationships of the two dyes.

FIG. 6 shows the excitation spectrum of DiA 611 and the excitation spectrum of Pacific Orange 621. Note that there is some overlap in the excitation spectra 611, 621, however, these dyes are still distinguishable and can be preferentially excited using appropriate light sources. Preferential excitement means that each dye can be excited without substantially exciting other dyes. DiA shows strong absorption at 445 nm and weak absorption at 405 nm. Conversely, Pacific Orange shows strong absorption at 405 nm and weak absorption at 445 nm. These wavelengths 405 nm and 445 nm can be produced using commercially available laser diodes. The emission spectra of both DiA 612 and Pacific Orange 622 are shifted to lower energy wavelengths and have a significant amount of overlap. As can be appreciated from FIG. 6, the fluorescent emission of both DiA and Pacific Orange can be detected in the wavelength range 620 from about 500 nm to about 650 nm.

As another example, the excitation 711, 721 and emission 712, 722 spectra of the Pacific Blue and SYTOX Blue dyes, respectively, are shown in FIG. 7. The excitation spectrum of Pacific Blue 711 shows strong absorption at 445 nm and weak absorption at 405 nm whereas the excitation spectrum of SYTOX Blue 721 shows the opposite behavior. The emission spectra of Pacific Blue 712 and the emission spectra of SYTOX Blue 722 indicate that both dyes can be detected in the wavelength range 620 from about 450 nm to about 530 nm. The dye combination of Pacific Blue and SYTOX is particularly interesting for multiplexed micro bead flow assays because this dye combination does not involve the red spectral range. Using the Pacific Blue/SYTOX Blue combination for micro bead identification leaves multiple wavelength options for detection of light emission from one or more fluorescent label dyes.

Figure 8:
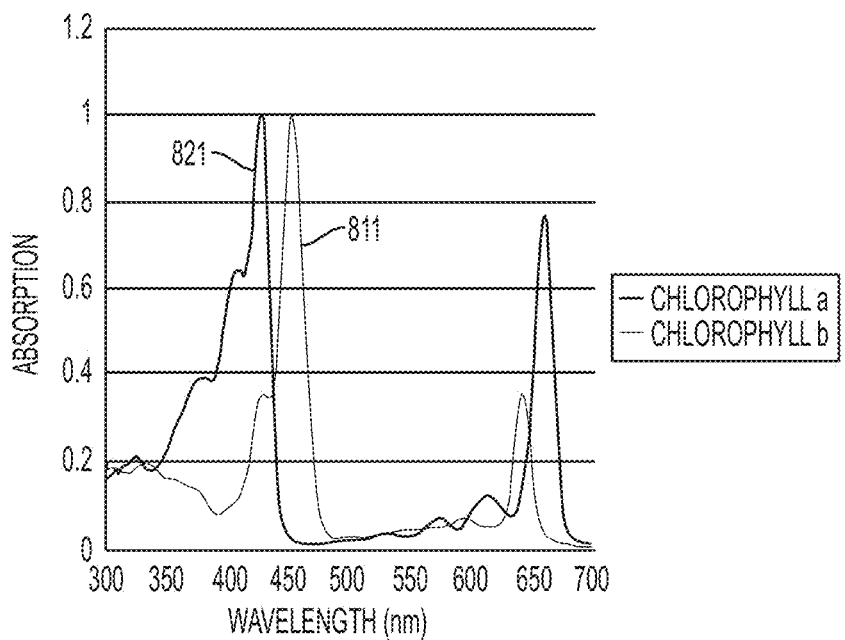
Figure 9:
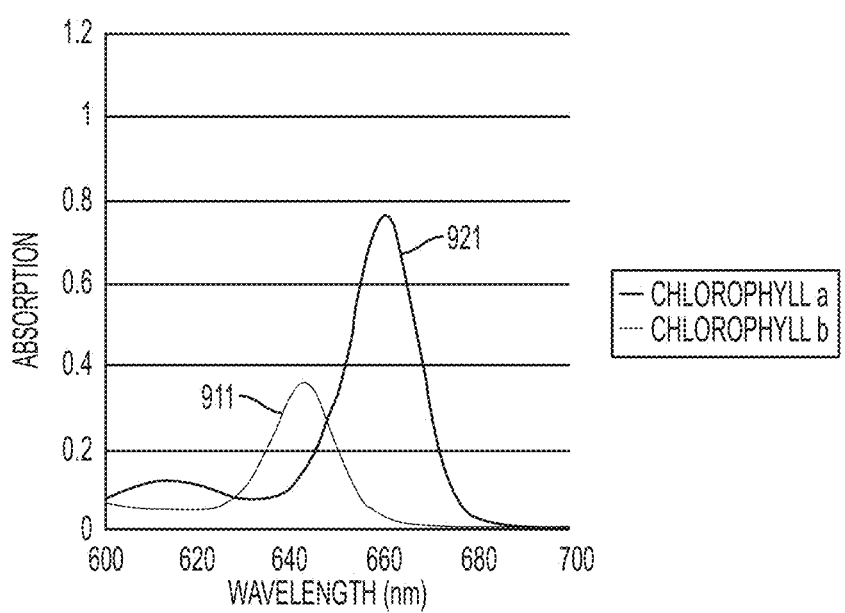
Figure 10:
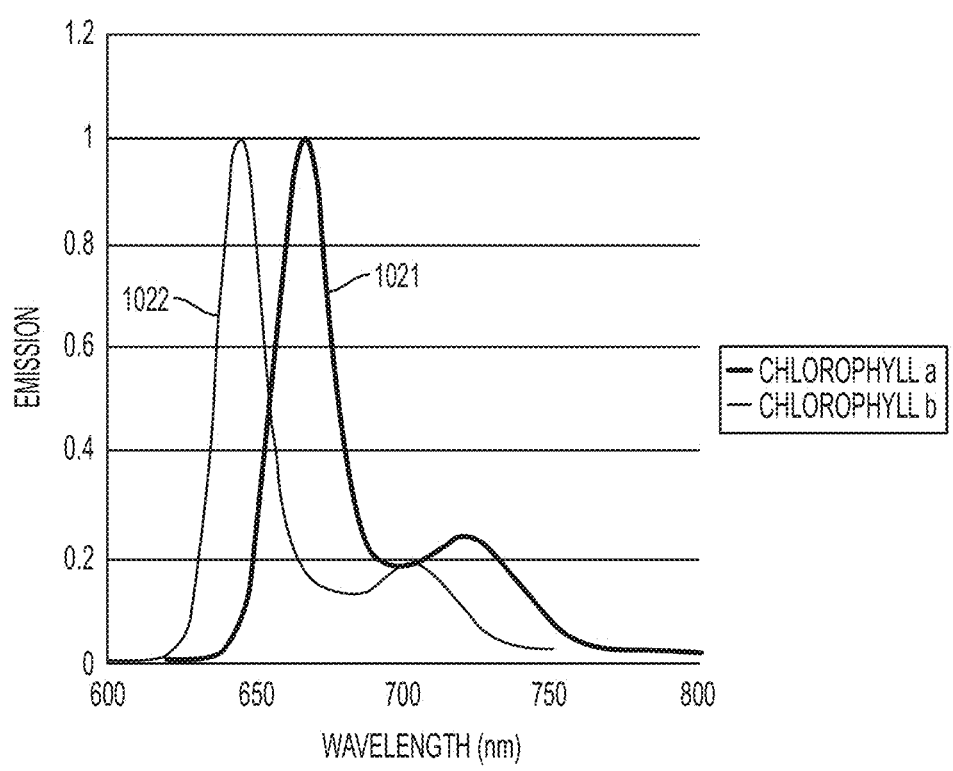

As yet another example, the excitation spectra 811, 821 and emission spectra 1012, 1022 of chlorophyll a and chlorophyll b dyes, respectively, are shown in FIGS. 8 and 10, respectively. The excitation spectrum of chlorophyll a 811 shows strong absorption at 450 nm and weak absorption at 430 nm whereas the excitation spectrum of chlorophyll b 821 shows the opposite behavior. FIG. 9 is an enhanced view of the excitation spectra of chlorophyll a and b in the 600 to 700 nm range. In this range, the excitation spectrum of chlorophyll a 911 shows strong absorption at 642 nm and weak absorption at 660 nm whereas the excitation spectrum of chlorophyll b 921 shows the opposite behavior—strong absorption at 660 nm and weak absorption at 642 nm. As shown in FIG. 10, the emission spectra of chlorophyll a 1021 and the emission spectra of chlorophyll b 1022 indicate that both dyes can be detected in a wavelength range of 625 to 725 nm.

The recognition elements that functionalize the micro beads can take a variety of forms, where the recognition elements interact in some way with the analytes of interest. For example, the recognition elements may comprise antibodies that bind specifically to certain antigens. In addition, each recognition element associated in some way with an additional dye referred to herein as a label. The recognition elements and/or the label dye may interact with each other, the analyte and/or one or more substances or molecules. Presence of an analyte may cause an increase or a decrease in light emanating from a micro bead. For example, in some implementations, one or more recognition elements may be associated with an additional dye, e.g., a fluorophor, such as a fluorophore-conjugated antibody, that increases light emission. In some implementations, one or more recognition elements may be associated with a quencher that decreases light emission from the label dye, such as quencher-conjugated competitor molecule.

In various embodiments, the presence, amount, and/or concentration of an analyte of interest can be determined by measuring the change in the light emission from an additional dye (also referred to as a label dye or tag) that is associated with one or more analytes of interest and/or with the recognition elements of the micro beads. The change in the light emission used to determine the amount and/or concentration of the analyte could occur in at least one of the following ways:

1) a fluorophore-conjugated antibody (i.e., an antibody conjugated with a label dye) binds to an analyte, which is bound to a micro bead causing an increase in light emanating from the micro bead when the analyte is present, 2) a fluorophore-conjugated antibody binds to a competitor molecule that is displaced from the recognition element of a micro bead by the analyte of interest causing a decrease in light emanating from the micro bead when the analyte is present, 3) a fluorophore-conjugated competitor molecule is displaced from the recognition element of a micro bead by the analyte of interest causing a decrease in light emanating from a micro bead when the analyte is present, and 4) a quencher-conjugated competitor molecule is displaced from a fluorophore-conjugated recognition element of a micro bead by binding the analyte of interest causing an increase in light emanating from the micro bead in presence of the analyte.

The above list is exemplary and non-limiting and the approaches discussed herein may be used with many techniques for changing light emanating from a micro bead based on presence, absence, amount, quantity, and concentration of analytes, particles, or other bits of matter.

Figure 11:
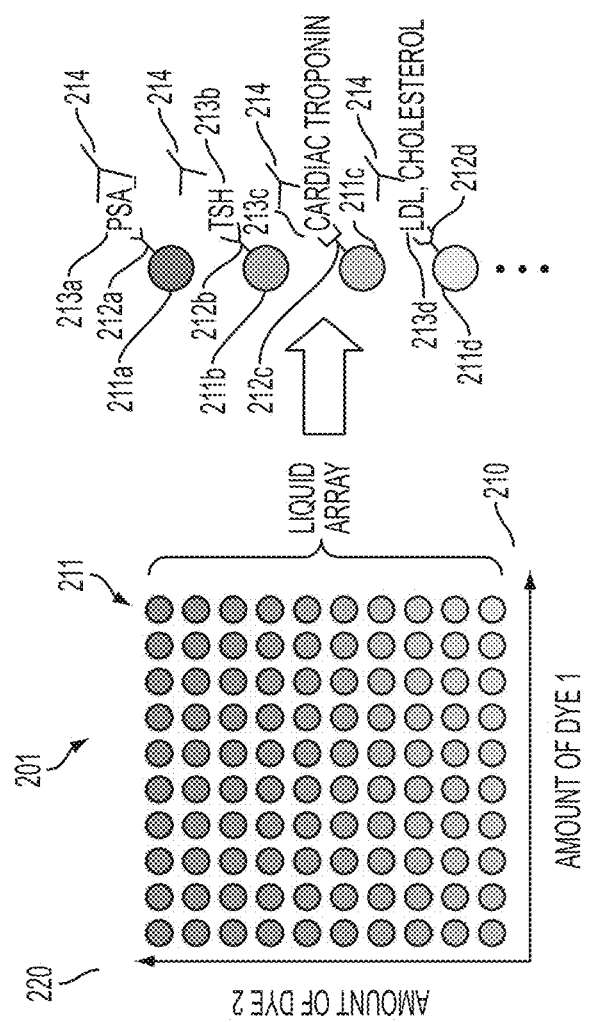
FIG. 11 shows an array of absorption-encoded micro beads functionalized with recognition elements.

FIG. 11 provides a graphical illustration for the first of the four scenarios discussed above. FIG. 11 shows the liquid array 201 of micro beads 211 of different types as in FIG. 2. At the right side of FIG. 11, some of the types of micro beads 211*a*-*d* are shown. Each type of the micro bead 211*a*-*d* is functionalized with a type of recognition element 212*a*-*d* configured to interact with and recognize a target analyte 213*a*-*d*. In this example, each recognition element comprises an antibody configured to bind to a certain antigen 213*a*-*d*.

Each type of recognition element 212*a*-*d* functionalizes a particular type of micro bead 211*a*-*d* and each micro bead type is identifiable by dyes in their characteristic proportional relationship for that micro bead type.

In the illustrated example, recognition element 212*a* of micro bead type 211*a* interacts with prostate specific antigen (SPA) 213*a*; recognition element 212*b* of micro bead type 211*b* interacts with thyroid stimulating hormone (TSH) 213*b*; recognition element 212*c* of micro bead type 211*c* interacts with cardiac troponin 213*c*; and recognition element 212*d* of micro bead type 211*d* interacts with low density lipoprotein (LDL) cholesterol 213*d*. In this example, the assay also includes one or more fluorophor-conjugated antibodies 214 that bind to the analytes 213*a*-*d* and serve as labels for the analytes 213*a*-213*d* that are bound to the micro beads 211*a*-211*d*. The fluorophor-conjugated antibodies 214 increase light emanating from the micro beads 211*a*-*d* when the analyte is present. The fluorophor-conjugated antibodies 214 can be stimulated to emit light and may have an absorption spectrum that is distinguishable from the absorption spectra of dye 1 and dye 2.

In some implementations, a separate type of fluorophor-conjugated antibody (referred to as a "tag" or "label") may interact with a specific analyte. For example, a first label may interact with a first analyte but not a second analyte and a second label may interact with a second analyte and not to the first analyte. In some implementations, as depicted in FIG. 11 and as discussed in various analyzer examples herein, one label 214 interacts with each target analyte 213*a*-*d*. In this example, the type of analyte can be discerned from the micro bead type, each micro bead type having a recognition element specific to a certain analyte. The presence and/or amount of analyte can be determined by stimulating the label dye, sensing the light emission of the label dye, and detecting an increase in the light emission, which indicates the presence of the analyte in this example. In other cases, the presence and/or amount of the analyte may be indicated by a decrease in the light emission from the label dye. For example, a decrease in the light emission from the tag may occur when the label dye, e.g., a fluorophore-conjugated antibody, binds to a competitor molecule that is displaced from the recognition element of the micro bead by the analyte of interest. Various implementations for detecting the presence, amount, and/or concentration of analytes may be implemented as set forth in scenarios 1-4 above.

The examples provided above are but some of the many different types of assays that can be used to detect the micro beads and/or the presence of analytes in a sample.

As previously discussed, each absorption-encoded micro bead type includes a number of dyes in a characteristic proportional relationship. The dyes have distinguishable absorption spectra but possibly similar emission spectra. This configuration enables identifying the type of micro bead using light of different emission spectra that overlaps the excitation spectra of the dyes. For absorption-encoded bead assays there are many methods possible to detect and identify the micro bead type. For instance, the absorption-encoded micro beads can be illuminated using light sources that emit light that is intensity modulated at different modulation frequencies. For example, if k dyes are used to encode the micro bead types, then k light sources may be used, wherein the intensity of the light emitted from each light source is modulated at a different frequency, $v_1, v_2, \ldots v_k$. The light emission from the dyes that encode the micro beads that is stimulated by the different light sources modulated at frequencies $v_1, v_2, \ldots v_k$ is also frequency-encoded by the modulation frequencies $v_1, v_2, \ldots v_k$. A photosensitive detector can be used to sense the time modulated light emission from the dyes and to generate an electrical detector signal. The detector signal can be evaluated to identify which types of micro beads are present in the sample. For example, the detector signal may be evaluated using FFT analysis to determine the proportional relationships of the dyes in the micro beads. The proportional relationships of the dyes can be extracted from the relative amplitude of the FFT peaks at the modulation frequencies of the light source that stimulates the dyes.

Note that the types and amounts of the dyes used to encode the micro beads are controllable, thus the light emission from the dyes can produce a relatively strong detector signal having a large signal to noise ratio (SNR). Based on this strong signal, it can be relatively easy to detect the micro beads in the sample and to distinguish between types of the absorption-encoded micro beads. Dyes used to label the analytes may produce a signal having a smaller SNR when compared with the signal produced by the absorption-encoded micro bead dyes. Thus, in some implementations, which are discussed in more detail below, it can be beneficial to sense the light emission from the micro bead encoder dyes using a first detector channel and to sense light emission from label dyes used to determine the presence, amount, and/or concentration of analytes using a second detector channel.

For simplicity of explanation, in some of the exemplary analyzers discussed herein, the number of dyes used to encode the micro bead types is equal to 2 (k=2). The presence of micro beads, identification of the micro bead type, and determination of speed, position, number, etc. of the micro beads can be accomplished by analyzers that include two light sources, e.g., lasers that provide light at two different excitation wavelengths. The excitation light emitted by each of the two light sources is intensity-modulated at different frequencies $\nu 1$ and $\nu 2$, respectively, e.g., in an excitation area in the flow channel.

Figure 12:
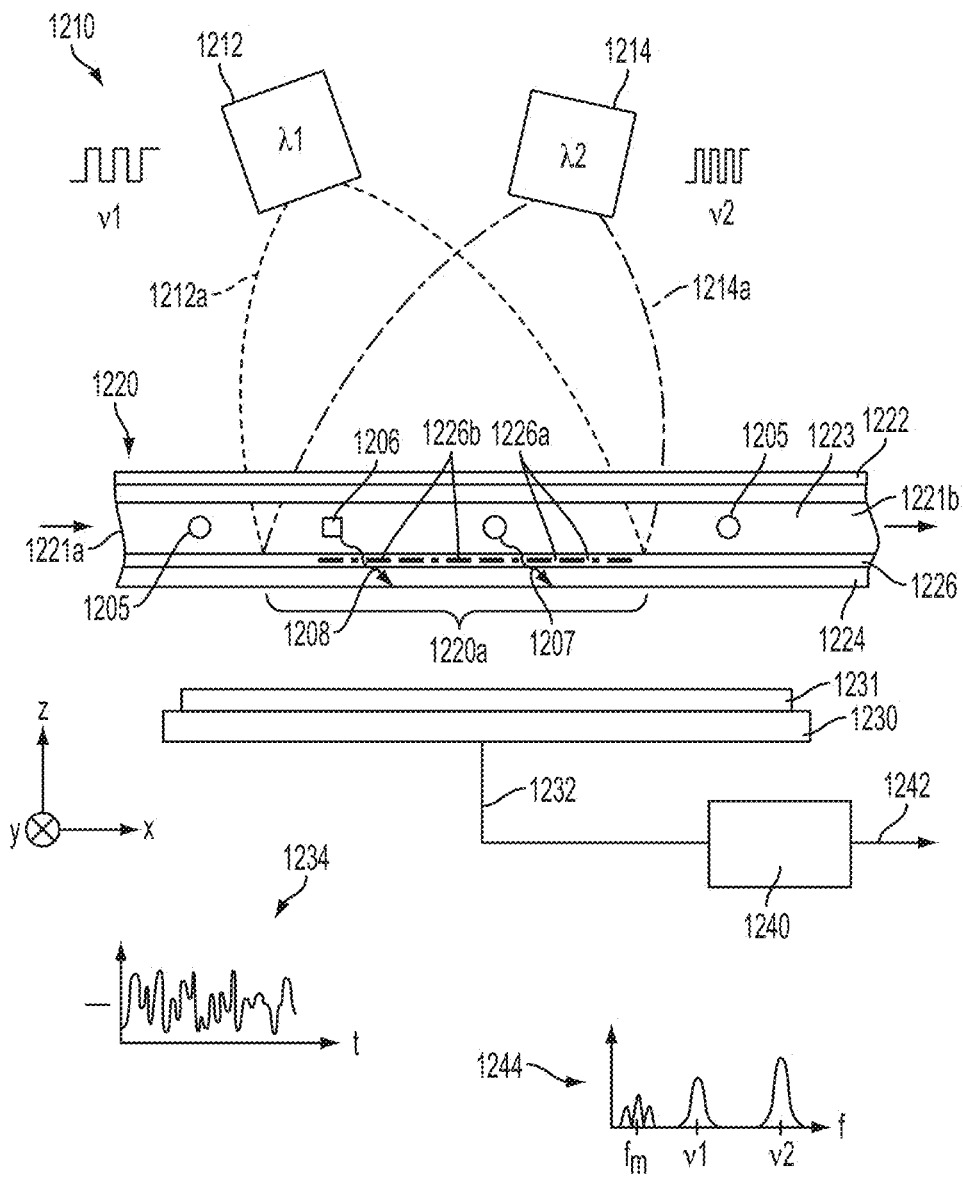
FIG. 12 is a schematic side or sectional view of a sample analyzer.

An example of a sample analyzer 1210 is shown schematically in FIG. 12. The analyzer 1210 can be used, for example, to identify absorption-encoded micro beads used to analyze a system, e.g., where sensing the presence of analyte is not necessarily part of the analysis. In some scenarios, the types of micro beads may correspond to a range of values for one or more micro bead characteristics, e.g., size, charge, shape, etc. The presence of certain types of micro beads in a sample that derives from or interacts with a system being evaluated can be used to analyze properties of the system. For example, as previously discussed, this type of analysis can be used to evaluate filter integrity or other system properties.

The analyzer 1210 includes light sources 1212, 1214, a fluid-handling device 1220, and a detector 1230. The fluidic device 1220 is adapted to receive a sample of interest to be analyzed. The sample may enter the device 1220 at an inlet 1221a thereof and exit the device 1220 at an outlet 1221b thereof, flowing generally along the x-direction through a flow channel 1223 formed between confining members 1222, 1224.

At least a portion of the confining member 1222 is transmissive to light emitted by the light sources 1212, 1214. In that regard, light source 1212 emits first excitation light in a first light beam 1212a, comprising a first wavelength $\lambda 1$, towards the fluidic device 1220, and light source 1214 emits second excitation light in a second light beam 1214a, comprising a second wavelength $\lambda 2$, towards the fluidic device 1220. The spectral makeup or composition of the excitation light emitted by the sources 1212, 1214 is preferably different enough from each other so that they preferably excite light emission from dyes that characterize different types of micro beads that are suspected to be present in the sample.

The confining member 1222 transmits both light beams 1212a, 1214a such that they illuminate the sample disposed within the flow channel 1223. FIG. 12 shows the excitation light beams illuminating substantially the same excitation portion 1220a of the flow channel 1223, i.e., complete overlap of the first and second excitation portions. System 1220 can be implemented with only partially overlapping or even non-overlapping excitation regions. The sample is depicted as containing two types of micro beads: micro beads 1205 of a first type, and micro beads 1206 of a second type, although a larger number of micro bead types can be used. Each micro bead 1205, 1206 is absorption-encoded by the first and second dyes (sometimes referred to herein as encoder dyes) according to its type, so that each type of micro bead has a characteristic proportional relationship of the first and second encoder dyes. The first excitation light 1212a preferentially excites the first encoder dye and does not substantially excite the second encoder dye. The second excitation light preferentially excites the second encoder dye and does not substantially excite the first encoder dye. Excitation of the first dye causes first light emission from the first dye. Excitation of the second dye causes second light emission from the second dye. Light 1207, 1208 emanating from the micro beads 1205, 1206 includes the first light emission and the second light emission according to the proportional relationship for the type of micro bead.

Light emitted by the first dye may or may not have a substantially different spectral composition from light emitted by the second dye. In many cases, any differences in spectral composition between light emitted from the various dyes are ignored by the photosensitive detector 1230 used in the analyzer 1210. The photosensitive detector 1230 in such cases may be designed to provide an output current, voltage, or other output signal that responds to the light impinging on the detector from, e.g., from light emission from one or both of the first dye and the second dye.

The confining member 1224, or at least a portion thereof, substantially transmits the emanating light 1207, 1208 originating from the excited dyes of the various micro beads 1205, 1206 in the flow channel 1223. The transmitted emanating light is thereafter intercepted by the photosensitive detector 1230, which converts the intercepted light into a current, voltage, or other measureable parameter. The photosensitive detector 1230 collects light emission from the dyes as the micro beads 1205, 1206 pass through a detection portion of the flow channel 1223. The detection portion of the flow channel 1223 overlaps at least in part with the excitation portion of the flow channel, i.e., with portion 1220a, and it may substantially coincide with such portion 1220a.

In order to help separate the light emission from the excited dyes of the micro beads 1205, 1206 from the typically much stronger or brighter excitation light from the light sources, an optical filter 1231 may be provided between the detector 1230 and the flow channel 1223. The optical filter 1231 preferentially blocks, e.g. by reflection, absorption, scattering, or any other known mechanism, the first and/or second excitation light 1212a, 1214a, and preferentially transmits light emanating from the excited dyes of the micro beads in the detection portion of the flow channel 1223 so that the signal to noise ratio (SNR) at the wavelengths of interest is increased. An optical filter such as optical filter 1231 is sometimes needed or desired to prevent the detector 1230 and/or its amplifier circuit(s) from experiencing saturation, and to allow lower noise detection of the light emission from the dyes. The optical filter 1231 may comprise a notch filter. Preferably, the notch filter will have wide transmission bands and narrow, strong rejection bands. Such filters maximize the spectral regions over which light emission from the dyes may occur, by narrowing the rejection bands to only the vicinity of the wavelengths of the excitation sources. Multiple notch filters having a variety of characteristics are available and could be used, the specific filter selected could be chosen to reject wavelengths outside the emission spectra of the dyes. In addition, one or more specific multi-notch filters for special combinations of excitation wavelength and dye combinations can be designed and fabricated. The use of suitable multiple notch filters gives an amount of freedom regarding the choice of the dyes because the dyes do not have to emit fluorescence in the same spectral region. Additionally, the dyes may be selected so that they have clearly different absorption at the selected excitation wavelengths in order to allow for a reliable differentiation between micro bead types.

Other techniques can also be used to reduce the amount of excitation light reaching the detector. For example, the excitation light may be directed along a path or axis that does not intersect the detector. In the case of FIG. 12, the filtered detector may be shifted to a position that is (from the perspective of FIG. 12) above or below the plane of the figure, such that a line drawn from the center of the detection portion of the flow channel to the center of the detector is parallel to the y-axis, and perpendicular to a line drawn from the center of either or both light sources to the center of the detection portion of the flow channel. Alternatively, the sources 1212, 1214 may be shifted to similar positions, such that the beams 1212a, 1214a are directed along axes that lie in the x-y plane rather than in the x-z plane, for example.

Detector 1230 generates an output on line 1232, which may be supplied to signal processing unit 1240. The line 1232 carries a time varying output signal, depicted schematically as output 1234. The signal processing unit 1240 may perform an analysis on the output signal 1234. In order to allow the signal processing unit 1240 to distinguish a signal component arising from light emission from the first dye and a signal component arising from light emission from the second dye, the sources 1212, 1214 are intensity modulated at different respective modulation frequencies $\nu 1$, $\nu 2$. The modulation allows the signal processing unit 1240 to identify signal components in the output signal 1234 associated with the dyes encoding micro beads of different types by evaluating the frequency content of the output signal 1234. The unit 1240 may, for example, calculate a Fourier transform, e.g., a discrete Fourier transform (DFT) (that may be calculated using a fast Fourier transform (FFT) algorithm), or other suitable frequency spectrum of the output signal 1234 or a portion thereof. Such a frequency spectrum is shown schematically as spectrum 1244 in FIG. 12.

Figure 13:
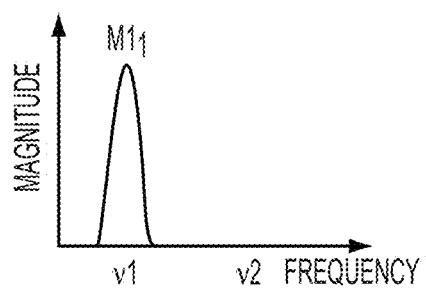
FIGS. 13-17 show Fourier transform spectra of fluorescent light emission for various dyes used in proportional relationships to identify micro bead types.
Figure 14:
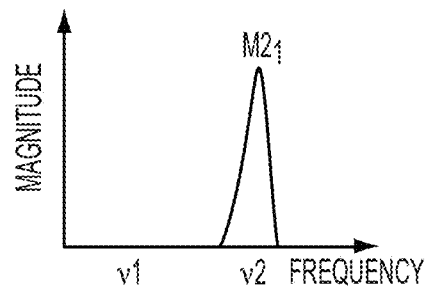
Figure 15:
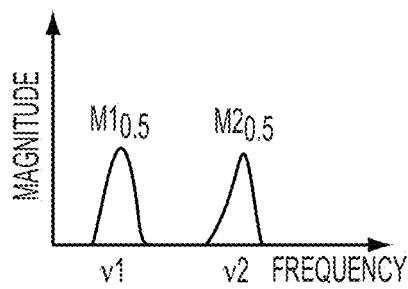
Figure 16:
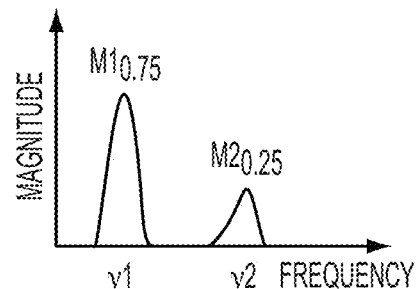
Figure 17:
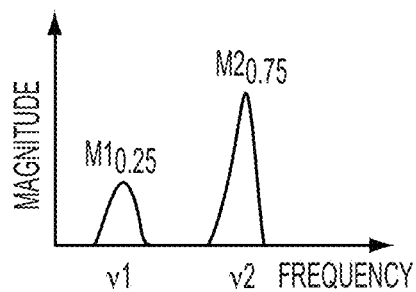

A frequency component at a frequency $f=\nu 1$ is indicative of the presence of a first dye and a frequency component at a frequency $f=\nu 2$ is indicative of the presence of a second dye. The proportional relationship of the dyes for a particular type of micro bead may be discerned from the magnitude of the components at $f=\nu 1$ and $f=\nu 2$ in the Fourier transform. FIGS. 13 through 17 show idealized Fourier transforms (magnitude vs. frequency) of light emitted from a two dye combination in various proportional relationships. For example, as shown in FIG. 13, a micro bead that has a proportional relationship of dye 1:dye 2 of 100%:0% may emit light at a nominal magnitude, $M1_1$, at $f=\nu 1$ and zero magnitude, $M2_0$, at $f=\nu 2$. As shown in FIG. 14, a micro bead that has a proportional relationship of dye 1:dye 2 of 0%:100% would emit light at a nominal magnitude, $M2_1$, at $f=\nu 2$ and zero magnitude, $M1_0$, at $f=\nu 1$. A micro bead that has a proportional relationship of dye 1:dye 2 of 50%:50% would emit light at a magnitude at $f=\nu 1$ of $M1_{0.5}=0.5M_1$ and a magnitude at $f=\nu 2$ of $M2_{0.5}=0.5M2_1$, as shown in FIG. 15. Light emission from micro beads having dye combinations with proportional relationships of dye 1:dye 2 of 75%:25% and 25%:75% are shown in FIG. 16 and FIG. 17, respectively.

Returning now to FIG. 12, note that multiple micro beads of one type or micro beads of different types may be present at the same time in the detection portion of the flow channel. Although the signal processing unit 1240 can be designed to be capable of detecting and identifying multiple micro bead types that are present within the detection portion, the analysis required may be fairly computationally intensive. In some embodiments, the number of micro beads of the various types in the sample are numerous, thus, it may be possible to rely only on detections of micro beads that are singly present in the detection portion for the analysis of the sample, and to ignore detections where multiple micro beads or multiple types of micro beads are present in the detection portion. In other words, the analyzer may be capable of discerning when these multiple micro bead events occur and to ignore these events.

Note also that the detection of a signal component at a given modulation frequency $\nu 1$ or $\nu 2$ does not by itself provide any information about the speed of the detected micro bead in the flow channel 1223, because detected signal components at those frequencies are independent of micro bead speed. However, at least in cases where the micro bead density is low enough so that only a single micro bead (at most) is likely to be present in the detection portion of the flow channel at any given time, or when multiple micro bead detections are ignored, then micro bead speed information may in some cases be obtained by measuring the time duration of the signal component associated with the micro bead, combined with information relating to the longitudinal dimension (i.e., the dimension along the direction of flow, or along the x-direction in FIG. 12) of the detection portion and/or the relevant excitation portion of the flow channel.

The analyzer 1210 of FIG. 12 may include an optional spatial filter 1226 that allows for additional and/or more precise information to be obtained regarding the micro beads. In some cases, the spatial filter 1226 may be in the form of a patterned mask. In some configurations, the spatial filter can be disposed between the flow channel 1223 and the detector 1230, denoted herein as an output spatial filter. In some configurations, the spatial filter can be disposed between the one or more of the light sources and the flow channel, denoted herein as an input spatial filter. One or more input spatial filters may be adapted to transmit light emitted, respectively, by the one or more light sources by varying amounts as the micro beads 1205, 1206 travel along the excitation portion of the flow channel 1223. In this configuration, the input spatial filter creates an excitation pattern of light in the excitation portion of the flow channel 1223. In some embodiments, one common input spatial mask serves to create the excitation pattern for all the light sources used. In some embodiments, each light source has an individual input spatial filter.

The input spatial filters discussed above are one way that components may be used in conjunction with the light sources to create the excitation pattern. According to various implementations, individual or collective masks, micro-optics, or patterned light sources can optionally be used to create the excitation pattern. The excitation pattern can be imaged and/or directed into the detection region using optical components for the imaging (e.g., lenses) and/or direction, (e.g., fiber optics or waveguides).

An output spatial filter 1226 is shown in FIG. 12 disposed between the micro beads 1205, 1206 in the detection portion of the flow channel and the photosensitive detector 1230. The output spatial filter is adapted to transmit light 1207, 1208 emanating from the micro beads 1205, 1206 in the flow channel 1223 by varying amounts as the micro beads 1205, 1206 travel along the detection portion of the flow channel 1223. In both cases of an input spatial filter and an output spatial filter, the variable transmission of light can be achieved with a longitudinal sequence or pattern of transmissive regions and non-transmissive regions as exemplified by transmissive regions 1226a and non-transmissive regions 1226b.

According to some embodiments of an input spatial filter, as a micro bead travels along the excitation portion of the flow channel, light emitted from the light sources is alternately transmitted to a micro bead and blocked from reaching the micro bead, the alternate transmission and non-transmission producing a distinguishable time-varying component in the time-varying output signal 1234. Unlike the time-varying components associated with the modulation of the light sources 1212, 1214 by frequencies ν1 and ν2, the additional time-varying component associated with the input spatial filter is dependent on the micro bead speed and position. Due to the presence of this additional modulation in the output signal 1234, additional frequency components disposed generally at a mask frequency $f_m$ would be present in the frequency spectrum 1244 of FIG. 12 if an input spatial filter were used.

According to some embodiments of an output spatial filter, as a micro bead travels along the detection portion of the flow channel, light emanating from the micro bead, due to light emission from excited dyes, is alternately transmitted to the detector 1230 and blocked from reaching the detector 1230. The alternate transmission and non-transmission of light from the dyes produces a distinguishable time-varying component in the time-varying output signal 1234. Unlike the time-varying components associated with the modulation of the light sources 1212, 1214, the additional time-varying component associated with an output spatial filter, such as output spatial filter 1226, is dependent on the speed and position of the micro bead. Due to the presence of this additional modulation in the output signal 1234, additional frequency components disposed generally at a mask frequency $f_m$ are depicted in the frequency spectrum 1244 of FIG. 12.

The output spatial filter 1226 is shown in FIG. 12 as being disposed between the flow channel 1223 and the detector 1230, and is shown disposed in close proximity to the flow channel. If desired, the spatial filter 1226 may be disposed at other positions, e.g., embedded within the confining member 1224, or disposed on the lower major surface (from the vantage point of FIG. 12) of the confining member 1224. Also, as previously mentioned a spatial filter may be positioned between one or more of the excitation light source(s) and the flow channel. The spatial filter 1226 may also be oriented differently along with the detector; for example, the spatial filter 1226 may be reoriented to reside in the x-z plane rather than in the x-y plane.

In some cases, rather than being disposed proximate to the flow channel, a spatial filter may be spaced apart from the flow channel. For example, an input spatial filter may be disposed between one or more of the light sources and the flow channel and one or more lens(es), mirror(s) and/or other imaging components may be used to image the spatial filter onto the flow channel so that the input spatial filter creates an imaged excitation pattern in the excitation area of the flow channel. An output special filter may also be located remotely from the flow channel. The remote output spatial filter still provides, from the standpoint of the detector, modulation of light emanating from moving micro beads. The imaging system provided by the lens(es), mirror(s), and/or other imaging components may introduce magnification, such that the actual or physical spatial filter is larger or smaller than its image at the flow channel in accordance with the magnification factor of the imaging system.

The pattern or sequence of transmissive regions 1226a and non-transmissive regions 1226b in the spatial filter 1226 define a transmission function that changes based on longitudinal position, i.e., based on position measured along the x-direction or flow direction. This transmission function may be substantially periodic, or it may instead be substantially non-periodic. An example of a periodic transmission function is a square wave, or a rectangle wave of constant period. A limitation of periodic transmission functions is that they do not typically allow for high spatial resolution of a micro bead. However, this limitation may be unimportant in cases where only a single micro bead is likely to be present in the detection portion of the flow channel at any given time or when data is only collected from events that include a single micro bead in the detection portion of the flow channel at any given time. Examples of this may include integrity testing of a filter system where typically only a few micro beads are detected. An advantage of a periodic transmission function is its ability to produce a clear, strong peak in the frequency spectrum (see e.g. spectrum 1244) of the detector output signal, for a single micro bead moving at a constant speed in the detection region.

Examples of a non-periodic transmission function are a random function, or a chirped function (having a monotonically increasing or decreasing period). An advantage of non-periodic transmission functions is that they do typically allow for high spatial resolution of a detected micro bead, by employing correlation techniques to determine the longitudinal position of the micro bead at a given moment in time. For example, a correlation may be carried out between the time-varying detector output 1234 and a signal template representative of the (non-periodic) transmission function. The presence and location of a peak in the correlation can be used to determine the precise position of the micro bead along the length of the spatial filter 1226. This capability can be used with higher micro bead densities in which multiple micro beads may be present in the detection portion of the flow channel at a given time. Note that for many multiplexed micro bead assays (assays that can be used to detect multiple analytes in a sample), it may be useful to use high micro bead concentrations to speed up the assay time. Transport of analyte to recognition elements on the micro beads can be a diffusion limited process and can take a relatively long period time for low analyte concentrations.

Note that the output spatial filter 1226, including the sizes of transmissive and non-transmissive regions 1226a, 1226b of the output spatial filter 1226, shown in FIG. 12 (and other spatial filters shown herein) are not necessarily shown to scale. In most cases, the "minimum feature size" (MFS) of a spatial filter would be on the order of the size of the micro beads. The MFS refers to the length, as measured along the longitudinal direction (i.e., the flow direction, e.g., the x-direction in FIG. 12), of the shortest identifiable region of the spatial filter. The shortest identifiable region may, in some cases, be a transmissive region, while in other cases it may be a non-transmissive region, while in still other cases it may be both a transmissive region and a non-transmissive region (i.e., if the shortest transmissive region has the same longitudinal length as the shortest non-transmissive region, or if all transmissive regions have the same longitudinal length as all non-transmissive regions). The MFS of the spatial filter used in an analyzer has a direct impact on the spatial resolution of the analyzer, with larger MFSs generally corresponding to lower spatial resolutions. Of course, the average or typical micro bead size also has an impact on spatial resolution. In many cases, it is desirable to design the spatial filter such that the MFS is on the order of the largest average micro bead size or somewhat greater, e.g., one to two times the average micro bead size for the largest micro bead type of interest to be detected.

The spatial filter 1226 may be substantially monochromatic, or it may be polychromatic as in the case of a color filter assembly. In a monochromatic spatial filter, the transmissive regions 1226a all have substantially the same transmission characteristic, and the non-transmissive regions 1226b also all have substantially the same transmission characteristic (but different from that of the transmissive regions). In a simple case, the transmissive regions 1226a may all be completely clear, as in the case of an aperture, and the non-transmissive regions 1226b may be completely opaque, as in the case of a layer of black ink or other absorptive, reflective, or scattering material. Alternatively, the transmissive regions 1226a may all have a given color or filter characteristic, e.g., high transmission for light emanating from excited micro beads, but low transmission for excitation light. Alternatively, the non-transmissive regions may have a low but non-zero light transmission, as in the case of a grey ink or coating, or a partial absorber or reflector.

In a polychromatic spatial filter, at least two different types of transmissive regions 1226a are provided: first transmissive regions having a first transmission characteristic, and second transmissive regions having a second transmission characteristic, each of these transmission characteristics being different from the (usually opaque or nearly opaque) transmission characteristic of the non-transmissive regions. The first transmission characteristic may correspond to a first filter type, and the second transmission characteristic may correspond to a second filter type. In cases where a first dye has an emission spectrum that is substantially different from that of a second dye, the transmission characteristics of the first and second transmissive regions can be tailored to preferentially transmit emanating light from the first or second dyes, respectively. For example, if the first dye emits light predominantly in the red region of the visible spectrum, and the second dye emits light predominantly in the green region of the visible spectrum, the first transmissive regions may have a higher transmission for red light than for green light, e.g., they may transmit red light and substantially block green light, and the second transmissive regions may have a higher transmission for green light than for red light, e.g., they may transmit green light and substantially block red light. In such cases, the first transmissive regions can be arranged in a periodic fashion with a first spacing or periodicity, and the second transmissive regions can be arranged in a periodic fashion with a different second spacing or periodicity. The different spacings or periodicities provided by the sets of different transmissive regions, together with the fact that the transmission characteristics of these regions are tailored to selectively transmit light emission from a particular dye, can be used to provide two distinct mask frequencies $f_{m1}$, $f_{m2}$ (refer e.g. to mask frequency $f_m$ in FIG. 12) in the frequency spectrum 1244 for the different constituent first and second dyes of the micro beads.

Regardless of which type of spatial filter 1226 is used, a given micro bead that is present in the detection portion of the flow channel may produce one, two, three, or more distinct signal components in the detector output 1234, and the signal components may appear as distinct frequency components in the frequency spectrum 1244. For example, if two dyes are used to encode the micro beads, a micro bead that includes 100% of dye 1 and 0% of dye 2 would produce one frequency component in the frequency spectrum 1244. As another example, a micro bead that includes 50% dye 1 and 50% dye 2 would produce two frequency components in the frequency spectrum. As yet another example, if two dyes are used to encode the micro beads and a spatial filter is used, three frequency components would typically be present in the frequency spectrum.

Thus, for k=2, one frequency component may occur at the modulation frequency of the excitation light source used to excite the first dye and another frequency component may occur at the modulation frequency of the excitation light source used to excite the second dye. These components are independent of the flow speed of the micro bead, and can be used to identify the micro bead type by matching the peak frequencies with the modulation frequencies of the sources and the magnitudes at the peak frequencies with the proportional relationship of the dyes characteristic of the type of micro bead.

A third frequency component preferably occurs at a substantially different frequency, referred to as the mask frequency $f_m$. This component can occur over a range of frequencies $f_m$ depending on the flow speed of the micro bead and the spatial frequency or periodicity of the spatial filter.

In most cases, the flow speed of the sample (and the micro beads it contains), the spatial frequency of the spatial filter 1226, and the modulation frequencies of the first and second light sources, $v1$ and $v2$, are selected such that $v1$ and $v2$ are both substantially greater than the range of possible frequencies for $f_m$. Such an arrangement allows the signal processing unit 1240 to identify micro bead type and to independently determine micro bead speed and/or position without interfering with each other. However, in some cases it may be acceptable or desirable for one or both of $v1$ and $v2$ to lie within the range of possible frequencies for $f_m$, or to be substantially less than such range of possible frequencies.

The analyzer 1210 of FIG. 12 illustrates an approach that is useful to detect the presence of micro beads and to identify various types of micro beads and/or to determine the speed and/or position of micro beads. In addition to detecting the presence of micro beads, types of micro beads, and/or the speed and/or position of the micro beads as discussed above, analyzers can be configured to determine a presence, amount and/or concentration of one or more analytes in the sample. As previously discussed, each type of micro bead may be functionalized to recognize a specific analyte. As also discussed above, in some cases, analyte presence, amount and/or concentration may be determined based on an increase or decrease in the light emission from an additional dye (referred to herein as label or tag dye) associated in some way with the recognition elements of the micro beads and/or with the analytes of interest. The label dye may comprise a fluorophor-conjugated antibody, or a fluorophor-conjugated competitor molecule, for example, as discussed elsewhere herein.

The label dye can have an absorption spectrum that is distinguishable from the absorption spectra of the dyes used to encode the micro beads. In some implementations, the label dye may also emit light at a wavelength that is discernible from the light emission from the dyes that encode the micro beads, but this need not be the case.

Figure 18:
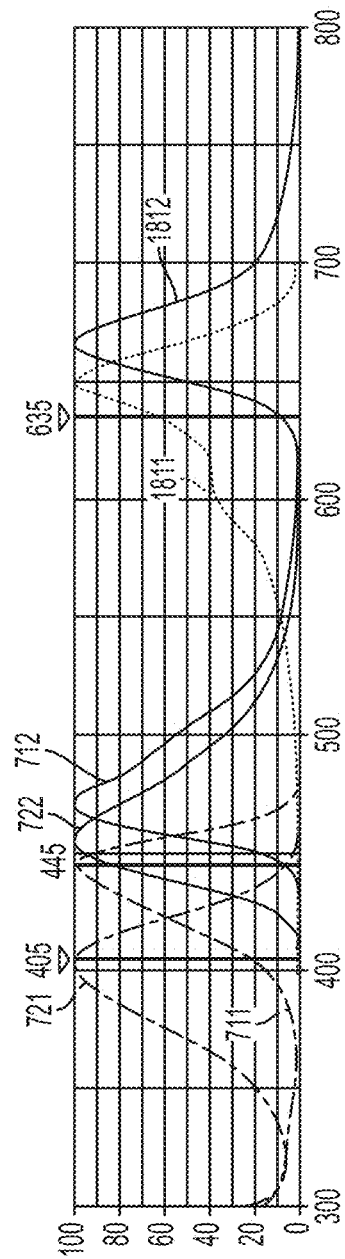
FIG. 18 is a set of graphs illustrating absorption and emission spectra for three dyes.

For illustration, FIG. 18 shows the example of the Pacific Blue/SYTOX dye combination (previously shown in see FIG. 7) for micro bead type differentiation in combination with Cy5 dye used as a label dye to indicate the presence of analyte. In this example, a first excitation light source can be used to emit first excitation light at 405 nm, which excites the Pacific Blue dye, and a second excitation light source can be used to emit second excitation light at 445 nm, which excites the SYTOX dye. The first excitation light can be intensity modulated at frequency ν1 and the second excitation light can be intensity modulated at frequency ν2. A third excitation can be used to emit third excitation light at 635 nm which is modulated at ν3 and which excites the Cy5 dye.

Excitation 1811 and emission 1812 spectra of the Cy5 dye is well separated from the excitation 711, 721 and/or emission spectra 712, 722 of the Pacific Blue and SYTOX dyes providing reduced cross talk and allowing for sensitive detection of the amount of antigen.

If the excitation light for each dye is intensity modulated at a different frequency, the emitted light from the dyes, represented by spectra 712, 722, and 1812, is frequency encoded. The frequency encoded light and can be detected and used to identify the micro bead type and the amount of antigen bound to the micro beads.

Figure 19:
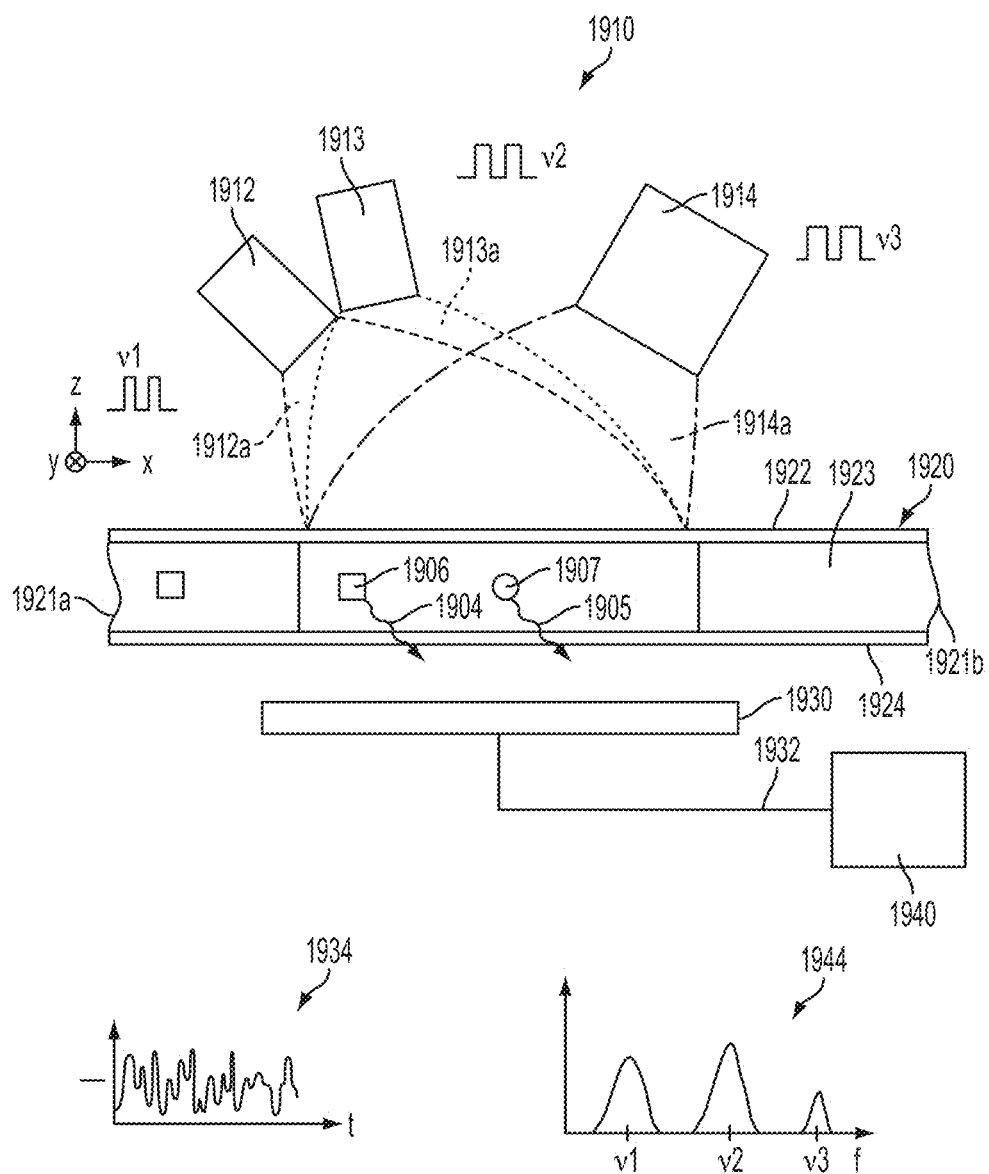
FIG. 19 is a schematic side or sectional view of another sample analyzer.

An illustrative sample analyzer 1910 for use with assays that involve detection of one or more micro bead types and detection of the presence of one or more analytes is shown schematically in FIG. 19, in the context of a Cartesian x-y-z coordinate system for reference purposes. The analyzer 1910 includes light sources 1912, 1913, 1914, a fluid handling device 1920, and a detector 1930. The fluidic device 1920 is adapted to receive a sample of interest to be analyzed. The sample may enter the device 1920 at an inlet 1921a and exit the fluidic device 1920 at an outlet 1921b, flowing generally along the x-direction through a flow channel 1923 formed between confining members 1922, 1924. The members 1922, 1924 may be or comprise plates or sheets of glass, plastic, or other suitable materials. One or both of members 1922, 1924 may be a microscope slide or a microscope cover glass, or portion thereof. The members 1922, 1924 need not, however, be planar in shape. For example, members 1922, 1924 may be portions of a unitary tube or pipe of circular cross section. Other non-planar shapes are also contemplated. In some cases, confinement of the sample may not be necessary, whereupon one or both of members 1922, 1924 may be omitted.

At least a portion of the confining member 1922 is transmissive to excitation light emitted by the light sources 1912, 1913, 1914. In that regard, light source 1912 provides first excitation light in a first light beam 1912a towards the fluidic device 1920, second light source provides second excitation light in a second light beam 1913a towards the fluidic device 1920, and third light source 1914 provides third excitation light in a third light beam 1914a towards the fluidic device 1920. Throughout this disclosure, the terms "first," "second," and "third" will be understood to be arbitrary terms used for identification purposes only, and are not intended to be limiting. The first excitation light comprises light of a first wavelength, $\lambda 1$, the second excitation light comprises light of a second wavelength, $\lambda 2$, and the third excitation light comprises light of a third wavelength, $\lambda 3$. The first excitation light may have a peak output at $\lambda 1$, the second excitation light may have a peak output at $\lambda 2$, and the third excitation light may have a peak output at $\lambda 3$. In most cases it is desirable for the excitation light from the sources to be relatively narrow band light, such as the light emitted by typical laser sources. However, extremely narrow bandwidth light (such as that of certain narrow line width laser sources) is not necessary in general. In some cases, for example, one or more of the light sources 1912, 1913, 1914 may comprise a conventional light emitting diode (LED) source or a resonant cavity LED (RC-LED) source, which may emit light in a bandwidth (measured in terms of full width at half maximum, or FWHM) of 5 to 60 nm, for example. If desired, the light sources 1912, 1913, 1914 may incorporate one or more filters to narrow or otherwise tailor the spectrum of the resultant output light.

Whichever light sources are selected, the spectral makeup or composition of the excitation light produced by the light sources 1912, 1913, 2114 is preferably different enough from each other so that they preferentially excite light emission from different dyes that may be present in the sample. To achieve this, in many cases it is desirable for the first excitation light to contain little or no light of the second wavelength $\lambda 2$ or the third wavelength $\lambda 3$, for the second excitation light to contain little or no light of the first wavelength $\lambda 1$ or the third wavelength $\lambda 3$, and for the third excitation light to contain little or no light of the first wavelength $\lambda 1$ or the second wavelength $\lambda 2$, and for $\lambda 1$, $\lambda 2$, and $\lambda 3$ to be sufficiently different from one another.

The confining member 1922 transmits light beams 1912a, 1913a, 1914a such that they illuminate the sample disposed within the flow channel 1923. The sample may contain a variety of types of micro beads, e.g., 100 or more types of micro beads, each micro bead being encoded with two or more encoder dyes in a characteristic proportional relationship that identifies the micro bead type. For simplicity of explanation, the example shown in FIG. 19 includes micro beads 1906 of a first type and micro beads 1907 of a second type, wherein each micro bead is encoded with two dyes. The first and second excitation light 1912a, 1913a excites the dyes encoding the micro beads 1906, 1907, according to their characteristic proportions as the micro beads 1906, 1907 move through the flow channel 1923. Third excitation light 1914a excites a label dye which labels analytes that have interacted with, e.g., have bound to, first and second recognition elements that functionalize the first and second micro beads 1906, 1907, respectively.

In some cases, the recognition elements that functionalize the micro beads 1906, 1907 are binding agents that bind a specific analyte to the micro bead. For example, the first type of micro bead 1906 may be functionalized with a first binding agent configured to bind to a first analyte and the second type of micro bead 1907 may be functionalized with a second binding agent configured to bind to a second analyte. The label dye binds to the both the first and second analytes. When the dyes are excited, light is emitted from the dyes encoding the micro beads and from the label dye that may be bound to a micro bead if the analyte of interest is present. Light emission from the encoder dyes may be analyzed to determine the type of micro bead and light emission from the label dye may be analyzed to detect the presence of analytes. The type of analyte can be determined from the type of micro bead. The light emission from the encoder and label dyes may or may not have substantially different spectral compositions. In most cases, any differences in spectral composition between light emanating from the various micro bead types to be detected are ignored by the photosensitive detector 1930 used in the analyzer 1910. The photosensitive detector 1930 in such cases may merely be designed to provide an output current, voltage, or other output signal that responds both to the amount of light impinging on the detector.

The confining member 1924, or at least a portion thereof, substantially transmits the light 1904, 1905 emanating from micro beads 1907, 1908, the emanating light 1904, 1905 comprising light emission from the excited dyes. The transmitted emanating light is thereafter intercepted by the photosensitive detector 1930, which converts the intercepted light into a current, voltage, or other measureable parameter. In exemplary embodiments, the detector 1930 is a single large area detector that provides only one output, such output varying in time in accordance with the light impinging on the active surface of the detector. In other cases, the detector may include a plurality or array of distinct photosensitive devices. In any case, the detector collects light emanating from dyes of micro beads that reside in a specific portion, referred to as a detection portion (which may be the same as or different from the excitation portion), of the flow channel 1923. The detection portion of the flow channel 1923 may be determined or defined as a function of the size and placement of the detector, design details of the flow channel, the presence of any lenses, mirrors, masks, apertures, or other optical components (not shown in FIG. 19) that may be placed between the detector and the flow channel, and so forth. The detection portion of the flow channel may overlap at least in part with the excitation portion of the flow channel. In some cases, the detection portion, and the excitation portion may all substantially coincide with each other. In some cases, there may be separate excitation portions, one excitation portion for each light source.

Exemplary photosensitive detectors that may be used in the disclosed systems, depending on the design specifications of the analyzer, include robust solid-state devices such as conventional photodiodes and avalanche photodiodes (APDs). Silicon photodiodes are responsive over a wavelength range from roughly 300 nm to 1.1 microns, and are plentiful, rugged, reliable, and relatively inexpensive. Numerous other types of photodiodes are also available, such as germanium, indium gallium arsenide (InGaAs), and extended-InGaAs, to name only a few. If desired, any other type of photosensitive detector may also be used, including, for example, one or more photomultiplier tubes. The detector may be of hybrid design, and in that regard may include one or more preamplifiers, thermoelectric coolers, and/or other features or capabilities.

Although not shown in FIG. 19, in some embodiments, a spatial filter, such as the input spatial filters and output spatial filters discussed in connection with the analyzer of FIG. 12 may be used in conjunction with the analyzer 1910.

Whichever type of detector 1930 is used, the detector generates an output on line 1932, which may be supplied to signal processing unit 1940. In a simple design, the line 1932 may be or comprise a coaxial cable, or a twisted pair of wires. The line 1932 carries a time varying output signal, depicted schematically as output 1932. The signal processing unit 1940 may perform an analysis on the output signal 1934. The analysis may include, for example, measuring correlation(s) (e.g., time domain or frequency domain correlations) with one or more other signals, and/or evaluating the frequency content of the output signal. The results of the analysis may be used to detect the presence of the micro beads and may distinguish types of the micro beads. Additionally, the results of the analysis may provide absolute or relative amounts of the different types of micro beads in the sample, speeds of the different types of micro beads and speed distributions of the micro beads. Based on the signal from the label dye, the presence of one or more analytes, the amounts of analytes and/or concentrations of the analytes in the sample, and so forth, may be determined. The signal processing unit 1940 may comprise one or more microprocessors and/or microcontrollers, and/or one or more application specific integrated circuits (ASICs), and/or one or more field-programmable gate arrays (FPGAs), and/or any other digital signal processing (DSP) circuitry. The signal processing unit may also optionally include volatile and/or non-volatile memory, storage device(s), and software. Software, hardware, and/or firmware may be tailored to carry out frequency analysis of time-varying signals, e.g., a set of instructions to carry out a fast Fourier transform (FFT) procedure or other Fourier transform or other transform procedure. Software, hardware, and/or firmware may be designed to carry out processes for comparing the time domain output signal to known signals or templates to determine the micro bead type and/or to detect the presence of analytes in the sample. The signal processing unit may also be configured to calculate an amount or concentration of various analytes in the sample based on detection of the micro bead types and detection of the analyte presence.

In some cases, the signal processing unit may be or comprise a desktop, laptop, notebook, or other portable or non-portable computer system, including e.g. mobile phones, smart phones, tablets, or any other type of personal digital assistant, suitably equipped with appropriate interfaces, networks, hardware, and software to carry out the desired signal analysis. The signal processing unit 1940 can include circuitry (hardware) configured to implement program steps (software) to implement one or more of the processes described herein including those illustrated in the flow diagrams of FIGS. 3, 4, 26, 27, and 29, for example.

In order to allow the signal processing unit 1940 to distinguish between signal components in the output signal 1934 due to light emission from the first dye that encodes the micro beads, signal components in the output signal 1934 due to light emission from the second dye that encodes the micro beads, and signal components in the output signal 1934 due to light emission from the label dye, the light sources 1912, 1913, 1913 are intensity modulated by drive signals at different respective modulation frequencies $v1$, $v2$, $v3$. The drive signals are preferably periodic. The drive signals may be substantial square waves or they may have duty cycles greater or less than 50% or they may have any other shape (e.g., sinusoidal or ramped) as desired. Preferably, however, the drive signal for light source 1912 contains a dominant frequency component at frequency $v1$, and the drive signal for light source 1913 contains a dominant frequency component at frequency $v2$, and the drive signal for light source 1914 contains a dominant frequency component at frequency $v3$. In this regard, a "dominant frequency" or "dominant frequency component" may refer to a frequency at which the Fourier signal power or other relevant frequency-based function exhibits a dominant peak, the dominant peak being greater in magnitude than all other function values of the frequency-based function, other than 1/f noise for frequencies approaching zero.

The intensity modulation of any one of the light sources may be accomplished directly or indirectly. In a direct modulation approach, a drive signal that powers or energizes the light source may be modulated, and the drive signal modulation may then directly translate into substantially the same modulation of the excitation light provided by the light source. Direct modulation is advantageous insofar as it typically requires no additional optical or mechanical parts, and is flexible and convenient. In an indirect approach, the light source may include a lamp or source in combination with a shutter device. The lamp or source in such cases may emit excitation light at a constant output level, and modulation may be provided by the shutter device. The shutter device may be mechanical, e.g. as in the case of a chopper wheel or a segmented scanning mirror, or it may be electro-optical with no moving parts, e.g. as in the case of a Kerr cell, Pockels cell, acousto-optic tunable filter (AOTF), or electro-optical modulator, for example.

The frequencies $v1$, $v2$, $v3$ are preferably selected to be slower than the frequencies associated with the characteristic response time of the respective sources 1912, 1913, 1914, so that the fluxes or intensities of the excitation light beams 1912*a*, 1912*b*, 1912*c* are modulated in substantially the same manner as the drive signals for the respective light sources. For example, if a given source has a characteristic response time of 10 ns, the drive frequency ν for that source is desirably less than 100 MHz (=1/10 ns). Moreover, the frequencies ν1, ν2, ν3 are also preferably selected to be slower than the characteristic response time of the light emission from the dyes (e.g. in the case of fluorescence, the 1/e fluorescent decay time τ), so that the fluxes or intensities of the light emission from the dyes are modulated in substantially the same manner, or at least in a similar manner, as the drive signals for the respective light sources and the excitation beams emitted by those sources. For example, if the light emission of a given dye a characteristic decay time of 1 μs, the drive frequency ν for the source responsible for the excitation of that dye is desirably less than 1 MHz (=1/(1 μs)). In some embodiments, at least one of frequencies ν1, ν2, ν3 may be zero or close to zero. In particular, in some cases, it may be helpful to improve SNR if the drive signal for the light source 1914 that excites the label dye has ν3=0. In order to provide optimal signal detection with minimal chance for signal misidentification, it is advantageous for the modulation frequencies ν1, ν2, ν3 to satisfy certain relationships beyond those discussed above.

In particular, it can be advantageous for the various modulation frequencies to not be related as harmonics. Additionally, the sum and/or difference frequencies of any of the modulating frequencies, ν1, ν2, ν3, and/or mask frequency, νm, should not interfere with any of the modulating frequencies, ν1, ν2, ν3, or the mask frequency, νm. In other words, the modulating and/or mask frequencies should be chosen so as not to cause problems for the data evaluation. Note that the lowest level or "baseline" for the drive signals, and for the associated modulated excitation beams and the emanating light from the micro beads, can be zero, but in general it need not be zero. Any given drive signal may oscillate between an upper level and a lower level, and the lower level may be zero or it may be an intermediate level between zero and the upper level. In the case of laser diode light sources, the use of an intermediate level above the laser threshold can achieve faster modulation speed and reduced wavelength chirp. Likewise, the flux or intensity of any given excitation beam may oscillate between an upper level and a lower level, and the lower level may be a completely dark or "off" state, or it may be an intermediate "on" state between the dark state and the upper level. Similarly, the flux or intensity of light emitted by any dye may oscillate between an upper level and a lower level, and the lower level may be a completely dark or "off" state, or it may be an intermediate "on" state between the dark state and the upper level.

In view of the fact that the detector 1930 may respond to light emission from the different dyes without any ability to inherently distinguish between such light emission, different frequencies of modulation of the drive signals for the light sources, is employed. The different frequencies of modulation of the drive signals causes these different frequencies to be present in the light emitted from the excitation sources, which in turn causes these different frequencies of modulation to be present the light emission from the dyes. In other words, the use of different modulating frequencies for the first, second, and third excitation light translates to different modulating frequencies of light emission from the first, second, and third dyes. The different modulating frequencies of light emission from the first, second, and third dyes allows the signal processing unit 1940 distinguish between signal components in the output signal 1934 associated with the first, second and third light emission from the first encoder dye, second encoder dye, and label dye, respectively. The unit 1940 may, for example, calculate a Fourier transform (e.g. using a Fast Fourier Transform (FFT) technique or other suitable technique) or other suitable frequency spectrum of the output signal 1934 or a portion thereof. Such a frequency spectrum is shown schematically as spectrum 1944 in FIG. 19. If the frequency spectrum includes a significant contribution (e.g. in the form of a local peak in the frequency spectrum) at a frequency ν equal to the modulation frequency ν of one of the light sources, that contribution corresponds to a signal component of the same frequency ν in the output signal 1934, which in turn is indicative of first, second or third light emission from the first or second encoder dyes or the label dye, respectively. In the case of analyzer 1910, a frequency component at a frequency f=ν1 is indicative of the presence and/or amount of a first encoder dye and first light emission. Similarly, a frequency component at a frequency f=ν2 is indicative of the presence and/or amount of a second encoder dye and second light emission. A frequency component at a frequency f=ν3 is indicative of the presence and/or amount of label dye and third light emission.

Information relating to the number or micro beads that are present in the flow channel at a given time, may be obtained by measuring the amplitude or strength of the signal components at the relevant frequencies, e.g., the amplitude of the frequency spectrum 1933 at the relevant frequencies ν1 and ν2 of the encoder dyes. Note that micro beads of different types may be present at the same time in the flow channel, and the signal processing unit 1940 will still be capable of distinguishing such micro beads based on the frequency evaluation or analysis of the output signal 1934. However, such analysis may require the use of a non-periodic spatial mask, as previously discussed herein, and/or may require significant computational resources to isolate the signals presented by the micro beads and then to perform frequency analysis and/or time correlations of the isolated signals. Thus, in assays that include a large number of micro beads of each type, it can be acceptable to ignore detection events that involve the presence of multiple micro beads in the detection region simultaneously or substantially simultaneously.

Once the type of micro bead has been identified by the presence and magnitude of the relevant frequency components (ν1 and ν2) of the light emission by the encoder dyes in the output signal 1934, presence of the analyte is indicated by an increase or decrease in the signal component in the output signal 1934 having frequency ν3. The type of micro bead (determined by ratio of ν1 and ν2) provides the analyte species (defined e.g. by the recognition element on the bead) and the magnitude of the FFT signal at ν3 from the label dye is a measure for the amount of analyte bound to a micro-bead. The amount of analyte can be determined from the amplitude of the FFT signal at ν3 for an individual bead. Measuring the amplitudes of the FFT signal at ν3 for a number of beads of each type, e.g., 100 or 1000 or more micro beads per bead type, and/or counting the number of micro beads of a particular type and/or performing statistical and/or other types of analysis on the micro beads increases the overall sensitivity and limit of detection (LOT) of the analyzer. Measuring the amplitudes of the FFT signal at ν3 for many micro beads (or many micro beads of each type) may also account for inhomogeneities in the sample.

For example, consider the scenario wherein micro beads of a first type are functionalized to recognize a first analyte and micro beads of a second type are functionalized to recognize a second analyte. If the first analyte is present in the sample, the first analyte interacts with the micro beads of the first type and the label dye labels the first analyte. After excitation by first excitation light 1912a from the first light source 1912, second excitation light 1913a from the second light source 1913, and third excitation light 1914a from third light source 1914, the first dye that encodes the first micro bead will emit a first light emission and the second dye that encodes the micro bead of the first type will emit a second light emission according to the proportional relationship characteristic of the micro bead type. The label dye will emit a third light emission that indicates the presence or absence of the first analyte. The signal strength of this light emission allows determining the amount of analyte.

If the second analyte is present in the sample, the second analyte interacts with the micro beads of the second type and the label dye labels the second analyte. After excitation by first excitation light from the first light source 1912, second excitation light from the second light source 1913, and third excitation light from third light source 1914, the first and second encoder dyes will emit first and second emission light according to the proportional relationship characteristic of the second micro bead type. The label dye will emit a third light emission that indicates the presence (and amount) or absence of the second analyte.

In various embodiments, the analyzer 1910 can be a system containing k light sources modulated at k distinct frequencies to detect at least n different micro bead types in a sample. For simplicity, k has been assumed to be 2 for this example. The reader will, however, readily appreciate that the analyzer 1910 can be extended in a straightforward way to cases in which k=3, 4, or more. Note that the number of micro bead types that can be differentiated can be greater than the number of modulated light sources included in the analyzer system. For example, even if the system includes only two light sources used for detecting the micro bead types, modulated at respective frequencies v1, v2, the system may employ analysis techniques to allow more than two micro bead types to be differentiated. For example, 100 or even more micro bead types are feasible with two light sources.

In order to enhance the detection performance, particularly of the v3 component, spatial masks can be included and spatial modulation techniques can be used. The use of spatial masks/spatial modulation can be used to determine the speed of the micro beads so as to increase the signal to noise discrimination and/or to increase the spatial resolution to deal with coincidences (two micro beads in the detection area at the same time). In addition, in some cases, more complex configurations including two detectors can be used as discussed herein. The stronger light emission from the encoder dyes modulated at v1 and v2 can be measured with a first detector, e.g., in a remote sensing configuration, whereas the relatively weaker light emission from the label dyes modulated at v3 can be detected using special filters and/or a spatial mask by a second detector, e.g., in a direct sensing configuration. These configurations are described in more detail below.

Figure 20:
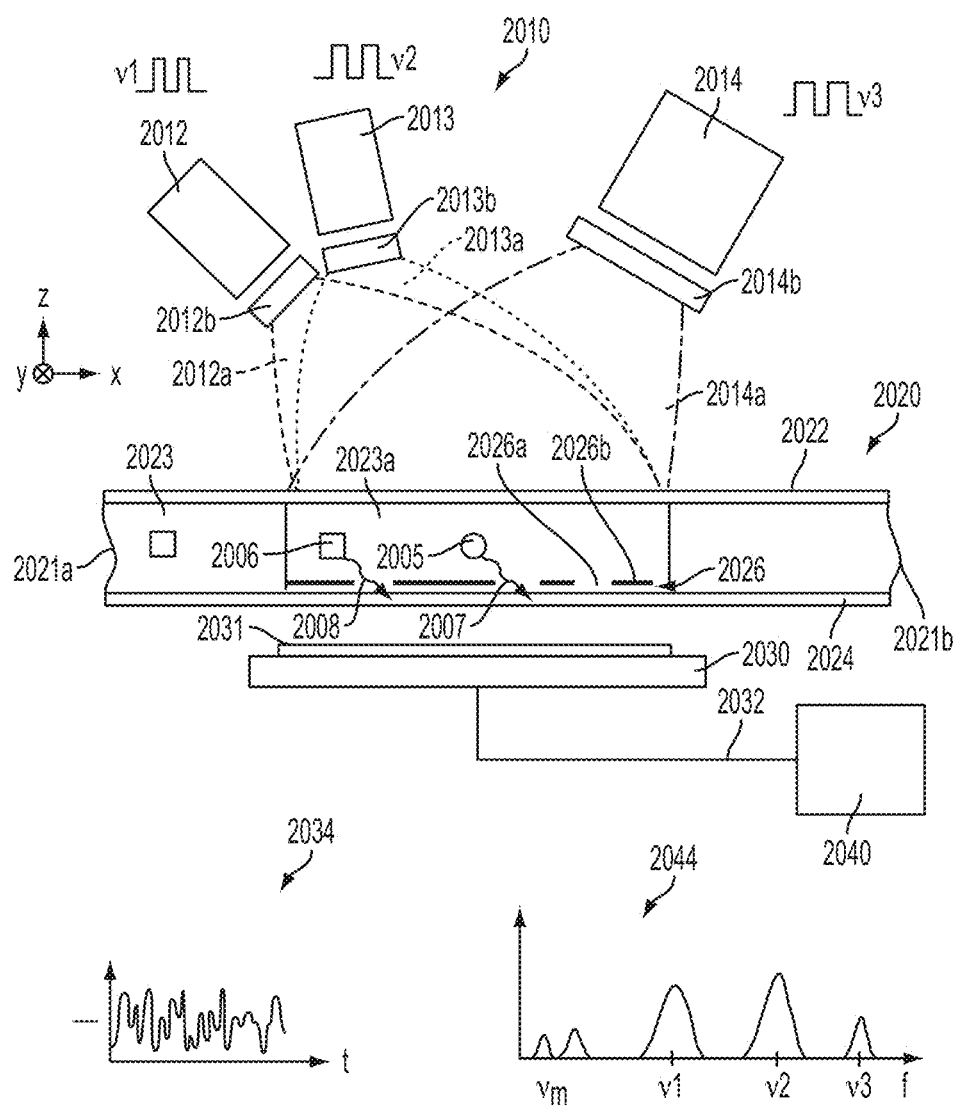
FIG. 20 is a schematic side or sectional view of a sample analyzer that includes a spatial filter.

Another sample analyzer 2010 is shown schematically in FIG. 20. The analyzer shown in FIG. 20 again, for simplicity of explanation, assumes a two dye combination for encoding the micro beads, although it will be appreciated that more dyes could be used to encode the micro beads in which case additional light sources could be used to detect the micro bead types. The analyzer 2010 is similar in many respects to the analyzer 1910 of FIG. 19, but with differences that will be discussed presently. For brevity, certain features of the analyzer of FIG. 19 and its components discussed above will be understood to apply to corresponding aspects and components of the analyzer 2010 of FIG. 20. For example, without limitation, features of the light sources and the modulation thereof, features of the flow channel, features of the photosensitive detector, and features of the signal processing unit will all be understood as applying equally to the analyzer 2010 of FIG. 20, unless otherwise indicated. More generally, features discussed in connection with any of the embodiments herein should be understood as also applying (as optional features or modifications) to all other disclosed embodiments, unless otherwise indicated.

Similar to analyzer 1910 of FIG. 19, the analyzer 2010 includes light sources 2012, 2013, 2014, a fluid handling device 2020, and a detector 2030. The fluidic device 2020 is adapted to receive a sample of interest to be analyzed. The sample may enter the device 2020 at an inlet 2021a thereof and exit the device 2020 at an outlet 2021b thereof, flowing generally along the x-direction through a flow channel 2023 formed between confining members 2022, 2024.

At least a portion of the confining member 2022 is transmissive to light emitted by the light sources 2012, 2013, 2014. In that regard, first light source 2012 emits first excitation light in a first light beam 2012a, comprising a first wavelength $\lambda 1$, towards the fluidic device 2020, second light source 2013 emits second excitation light in a second light beam 2013a, comprising a second wavelength $\lambda 2$, and third light source 2014 emits third excitation light in a third light beam 2014a, comprising a third wavelength $\lambda 3$, towards the fluidic device 2020. The spectral makeup or compositions of the excitation light emitted by the sources 2012, 2013, 2014 are preferably different enough from each other so that they preferentially excite light emission from different dyes that are suspected to be present in the sample.

The confining member 2022 transmits light beams 2012a, 2013a, 2014a such that they illuminate the sample disposed within the flow channel 2023. The sample is depicted as containing two types of micro beads: micro beads 2005 of a first type, and micro beads 2006 of a second type. It will be understood that with two dyes many more micro bead types could be present in the sample and these micro bead types would be identifiable by the presence of the two dyes in each micro bead type in a characteristic proportional relationship for that micro bead type. The first excitation light preferentially excites the first dye used to encode the micro beads 2005, 2006. The second excitation light preferentially excites the second dye used to encode the micro beads 2005, 2006. The third light source preferentially excites a label dye used to detect the presence of an analyte in the sample. Light 2007 emanates from the micro beads 2005 of the first type. Light 2007 may include components of light emission from the first dye, light emission from the second dye and/or light emission form the third (label) dye. Light 2008 emanates from the micro beads 2006 of the second type. Light 2008 may include components of light emission from the first dye, light emission from the second dye and/or light emission form the third (label) dye.

Just as mentioned above in connection with FIG. 19, light emission from the first encoder dye may or may not have a substantially different spectral composition from light emission from the second encoder dye that may or may not have substantially different spectral composition from light emission from the label dye. In many cases, any differences in spectral composition between light emanating from the various dyes are ignored by the photosensitive detector 2030 used in the analyzer. The photosensitive detector 2030 in such cases may merely be designed to provide an output current, voltage, or other output signal that responds both to the amount of light impinging on the detector from the first micro bead(s), and to the amount of light impinging on the detector. This technique can of course also be combined with multicolor detection (typically realized with multiple detectors with different dichroic mirror and/or filter combinations). This increases the complexity of the system but may provide more sensitive detection of analytes among other uses.

The confining member 2024, or at least a portion thereof, substantially transmits the emanating light originating from the various excited dyes included in a micro bead in the detection portion of the flow channel. The light emission from the micro beads is intercepted by the photosensitive detector 2030, which converts the intercepted light into a current, voltage, or other measureable parameter. The detector collects light emanating from micro beads residing in a specific portion, referred to as a detection portion, of the flow channel. The detection portion of the flow channel may overlap at least in part with the excitation portion of the flow channel, i.e., with portion 2023*a*, and it may substantially coincide with such portion 2023*a*.

As previously discussed, in order to help separate the light emitted from the dyes from the typically much stronger or brighter excitation light from the light sources, an optical filter 2031 may be provided between the detector 2030 and the flow channel 2023. The optical filter 2031 may substantially block the first, second, and third excitation light 2012*a*, 2013*a*, 2014*a*, and substantially transmit light emission from one or more of the dyes.

Similar to FIG. 19, the detector 2030 generates an output on line 2032, which may be supplied to signal processing unit 2040. The line 2032 carries a time varying output signal, depicted schematically as output 2034. The signal processing unit 2040 may perform an analysis on the output signal 2034, which analysis may be the same as or similar to the analysis discussed in connection with FIG. 19. In order to allow the signal processing unit 2040 to distinguish between signal components in the output signal 2034 due to the first and second dyes and the label dye the sources 2012, 2013, 2014 are modulated at different respective modulation frequencies ν1, ν2, ν3. The different modulation allows the signal processing unit 2040 to distinguish between signal components in the output signal 2034 from the first light emission from the first dye, second light emission from the second dye and third light emission from the third dye. Distinguishing between these signal components allows the processing unit to discern relationships of the encoder dyes indicative of the micro bead type and to detect the label dye by evaluating the frequency content of the output signal 2034. The unit 2040 may, for example, calculate a Fourier transform or other suitable frequency spectrum of the output signal 2034 or a portion thereof. Such a frequency spectrum is shown schematically as spectrum 2044 in FIG. 20. A frequency component at a frequency f=ν1 is indicative of the presence of the first dye in the detection portion 2023*a* of the flow channel 2023, a frequency component at a frequency f=ν2 is indicative of the presence of the second dye in the detection portion 2023*a* of the flow channel 2023. The relative magnitudes of the signals at f=ν1 and f=ν2 is indicative of the proportional relationship that characterizes each type of micro bead. A frequency component at a frequency f=ν3 is indicative a label dye associated with the presence of one or more analytes.

The analyzer 2010 of FIG. 20 includes a spatial filter 2026 that allows for improved signal to noise discrimination and additional or more precise information to be obtained regarding the dyes that encode the micro beads and/or the label dyes associated with the analytes of interest in the sample. FIG. 20 shows several potential optional locations for the spatial filter. In one arrangement, an output spatial filter 2026 may be located between the micro beads and the detector. In another optional arrangement, an input spatial filter 2012*b*, 2013*b*, 2014*b* may be located (along with other optical elements) in the path of the light emitted by one or more of the light sources. In some cases, the pattern of the input spatial filter may be imaged onto the flow path by an optical element such as a lens, however, in most cases, the preferred filter location is close to the flow channel 2023 itself as shown in FIG. 20.

In some cases, the input or output spatial filter may be in the form of a patterned mask. A patterned mask 2026 may be adapted to transmit light emanating from the excited micro beads in the flow channel by varying amounts as the micro beads travel along the detection portion of the flow channel. This variable transmission is preferably achieved with a longitudinal sequence or pattern of transmissive regions 2026*a* and non-transmissive regions 2026*b*.

As an excited micro bead travels along the detection portion of the flow channel, light emanating from such micro bead is alternately transmitted to the detector 2030 and blocked from reaching the detector 2030, the alternate transmission and non-transmission producing another distinguishable time-varying component in the time-varying output signal 2034. Unlike the time-varying light components associated with the modulation of the light sources 2012, 2013, 2014, the additional time-varying component associated with the spatial filter 2026 is dependent on the speed, and position, of the micro bead. Due to the presence of this additional modulation in the output signal 2034, additional frequency components disposed generally at a mask frequency $f_m$ are depicted in the frequency spectrum 2044 of FIG. 20.

As is evident from FIG. 20, the pattern or sequence of transmissive regions 2026*a* and non-transmissive regions 2026*b* in the spatial filter 2026 define a transmission function that changes based on longitudinal position, i.e., based on position measured along the x-direction or flow direction. This transmission function may be substantially periodic, or it may instead be substantially non-periodic.

FIG. 20 illustrates several optional arrangements for a spatial filter. According to some aspects, the spatial filter may be arranged as illustrated by spatial filter 2026, such that the spatial filter 2026 is disposed between the excitation region 2023*a* of the flow channel 2023 and the detector 2030. According to some aspects, one or more optical elements 2012*b*, 2013*b*, 2014*b*, e.g., spatial filters, color filters, lenses, etc., may be arranged between one or more of the light sources 2012, 2013, 2014 and the excitation region 2023*a* of the flow channel 2023. In some implementations, one or more of the optical elements 2012*b*, 2013*b*, 2014*b* may be or comprise a spatial filter. If a spatial filter is used in this arrangement, the pattern of the spatial filter masks the excitation light such that the mask pattern is imaged onto the excitation region 2023*a*. Each light source 2012, 2013, 2014, may have an associated spatial filter 2012*b*, 2013*b*, 2014*b* or, possibly with the use of appropriate optical elements, e.g., a lens arrangement, a single spatial filter may serve to mask all light sources.

The optical elements 2012*b*, 2013*b*, 2014*b* may comprise other optical elements instead of, or in addition to a spatial filter. For example, one or more of the optical elements 2012*b*, 2013*b*, 2014*b* may be or comprise a color filter, such as a narrow band color filter that is associated with (paired with) a broad band light source. The narrow band color filter restricts the wavelengths generated by the broad band light source to a band of wavelengths near the excitation range of a dye in the sample. According to some implementations, the one or more of the optical elements 2012*b*, 2013*b*, 2014*b* may be or comprise a lens. For example the lens may be used to focus the excitation light emitted by an associated light source 2012, 2013, 2014 onto the excitation area. According to some aspects, one or more lenses may be used in combination with one or more spatial filters (or other type of filter) to image the spatial filter(s) onto the flow channel.

Regardless of which type of spatial filter is used or the arrangement of the spatial filter with respect to the light source(s), the flow channel, and the detector, for a two encoder dye combination, k=2, a given micro bead that is present in the detection portion of the flow channel may produce typically four or more distinct signal components in the detector output 2034, which signal components may appear as distinct frequency components in the frequency spectrum 2044. Two of these components occur at the modulation frequencies of the excitation light sources associated with encoder dyes in the proportional relationship that characterizes the type of micro bead. These frequency components can be used to identify the type of micro bead and are independent of the flow speed of the micro bead. The micro bead type can be identified by analyzing the magnitude of the FFT at the modulation frequencies of the first and second excitation light sources and determining the proportional amounts of the emission light that is contributed from each of the dyes.

Another signal component or frequency component preferably occurs at a substantially different frequency than the frequency component associated with the intensity modulation of the excitation light sources that identifies the micro bead type, and is instead associated with the intensity modulation of the light that excites the label dye. This component of the emission light can be used to determine a presence and/or amount of analyte recognized by the micro beads and is independent of micro bead speed.

Another signal component or frequency component preferably occurs at a substantially different frequency from any of the signal components described above, and is referred to as the mask frequency $f_m$. This component can occur over a range of frequencies $f_m$ depending on the flow speed of the micro bead and the spatial frequency or periodicity of the spatial filter.

Figure 21:
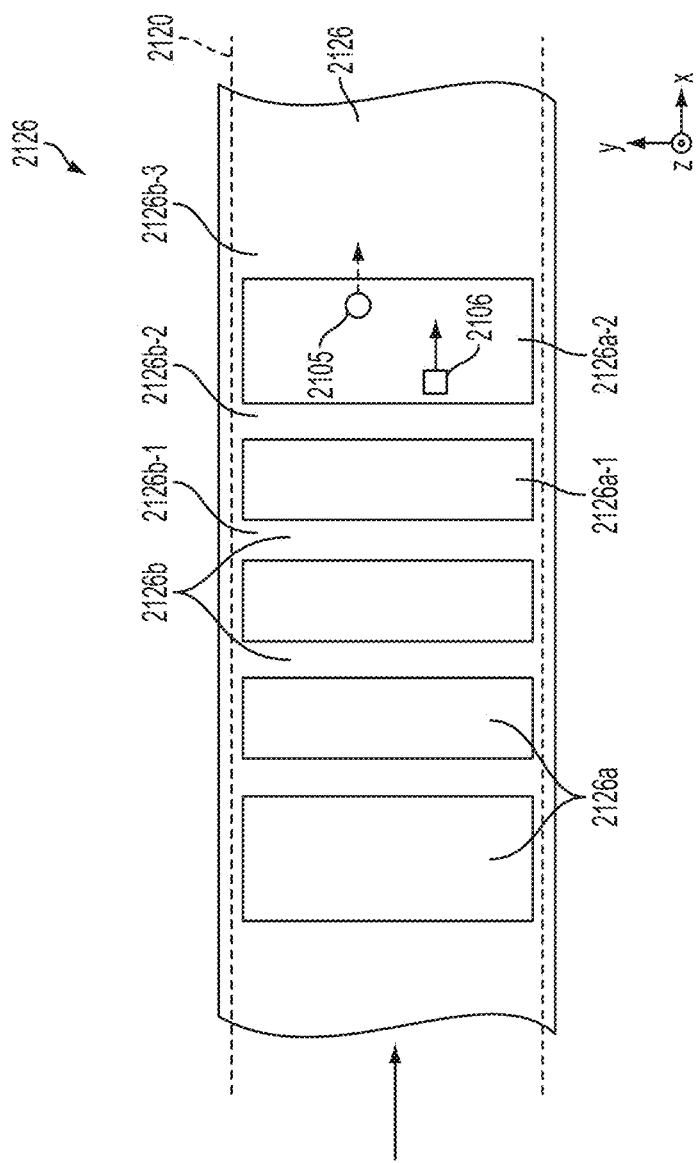
FIG. 21 is a schematic plan or front view of a spatial filter for use in the disclosed analyzers.

Turning now to FIG. 21, we see there a schematic plan or front view of a representative spatial filter 2126 that may be used in the disclosed analyzers. The filter 2126 may be remotely positioned between a light source and the micro beads of interest or may be positioned between the micro beads of interest and the detector, for example. The spatial filter 2126, which may in some cases be a magnified or de-magnified image of a remotely positioned spatial filter selectively masks light emanating from micro beads within the flow channel of a fluid handling device. First and second micro beads 2105, 2106 are shown to be disposed behind the spatial filter 2126, traveling in a flow direction generally parallel to the x-axis. The spatial filter 2126 comprises transmissive regions 2126a and non-transmissive regions 2126b arranged in a pattern along the longitudinal direction. In a simple case, the filter may be an extended film or layer of opaque material in which a number of apertures have been formed. The apertures may correspond to the transmissive regions 2126a, and the non-transmissive regions 2126b may correspond to the undisturbed opaque material. The longitudinal dimensions (lengths) of the alternating transmissive regions 2126a and non-transmissive regions 2126b determine the transmission as a function of position along the x-axis. As discussed above, this transmission function may be substantially periodic or non-periodic. The spatial filter 2126 may also be substantially monochromatic, or instead polychromatic.

Figure 22:
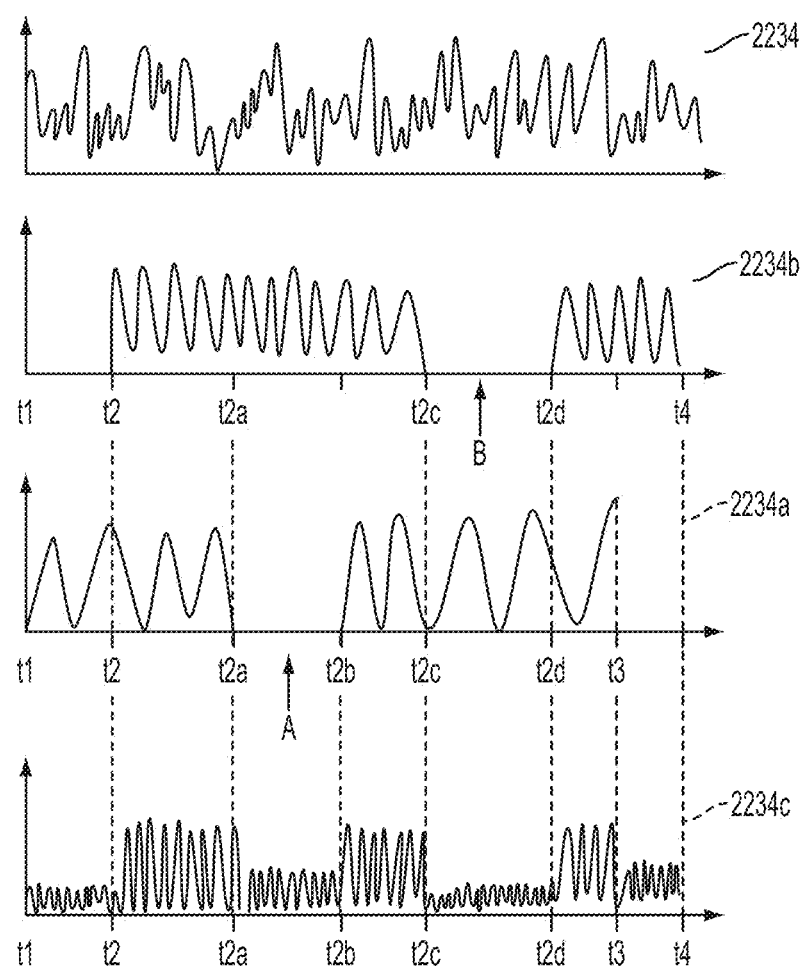
FIG. 22 is a group of graphs that depict idealized signals vs. time to assist the reader's understanding of the disclosed techniques, the group including an idealized graph of a representative detector output signal, and idealized graphs of constituent signal components associated with two micro bead types.

FIG. 22 is a group of graphs that, in conjunction with FIG. 21, depict idealized signals to assist the reader's understanding of some of the disclosed techniques to detect the speed and/or presence of micro beads. In this example, two dyes are used to characterize the micro bead types and to simplify the explanation, the micro beads discussed in this example are a first micro bead type having a proportional relationship of the two dyes of 100% of the first dye and 0% of the second dye. The second micro bead type discussed in this example is characterized by the two dyes in a proportional relationship of 0% of the first dye and 100% of the second dye. It will be understood from reading this disclosure that other proportional relationships could be used for other micro bead types.

In the uppermost graph of FIG. 22, a representative time-varying detector output signal 2234 is shown. The signal 2234 may appear on the output of a detector positioned to receive light transmitted by the spatial filter 2026 of FIG. 20, as used in a system having modulated light sources such as that of FIG. 20. The lower graphs of FIG. 22 show possible constituent signal components 2234a, 2234b, and 2234c that are combined with other signal components to form the signal 2234. The signal 2234a represents the signal component provided by a first type of micro bead and the signal 2234b represents the signal component provided by a second type of micro bead, and the signal component 2234c represents the signal component provided by a label dye that is bound to both the first and second micro beads 2105 and 2106 of FIG. 21.

The signal 2234a begins at a time t1 and ends at a time t3. At the time t1, the first micro bead passes from non-transmissive region 2126b-1 into transmissive region 2126a-1 of the spatial filter 2126. During the time period labeled "A", a micro bead of the first type passes behind non-transmissive region 2126b-2. At time t3, the micro bead passes from the transmissive region 2126a-1 to the non-transmissive border region 2126b-3. The first micro bead 2105 thus is present in the detection region of the flow channel at time t1 and exits the detection region at time t3. The high frequency modulation that can be seen in the signal 2234a in the time windows corresponding to the transmissive regions 2126a-1 and 2126a-2 represents the variability in the emanating light from the first encoder dye as a result of the modulation of the corresponding light source, e.g., the first light source 2012 of FIG. 20.

The signal 2234b represents the signal component provided by the second type of micro bead 2106 (see FIG. 21). The signal 2234b begins at a time t2 and ends at a time t4. At the time t2, the second micro bead 2106 passes from non-transmissive region 2126b-1 into transmissive region 2126a-1 of the spatial filter 2126. At the time labeled "B", the micro bead 2106 passes behind the non-transmissive region 2126b-2 that separates the last two transmissive regions 2126a-1, 2126a-2. At time t4, the micro bead 2106 passes from the final transmissive region 2126a-2 at the downstream end of the spatial filter 2126 to the non-transmissive border region 2126b-3. The second micro bead 2106 thus is present the detection region of the flow channel at time t2 and exits the detection region at time t4. The high frequency modulation that can be seen in the signal 2234b in the time windows corresponding to the transmissive regions 2126a represents the variability in the emanating light from the second encoder dye as a result of the modulation of the corresponding light source, e.g., the second light source 2013 of FIG. 20.

Signal 2234c represents the signal corresponding to the label dye that is bound to both the first and second micro bead 2105, 2106. During the time period from t1 to t2, the amplitude of signal component 2234c corresponds to the amount of label dye bound to the first micro bead 2105 that is within a transmissive region 2126a-1 of spatial filter 2126. During the time period from t2 to t2a, signal component 2234c corresponds to the amount of label dye bound to the first micro bead 2105 and/or the second micro bead 2106. During time period t2a to t2b, the first micro bead 2105 is behind non-transmissive region 2126b. Thus, during time period t2a to t2b, the amplitude of signal component 2234c indicates an amount of analyte bound to the second micro bead 2106. During the time period from t2b to t2c light emanating from first and second micro beads is not blocked by a non-transmissive region of the spatial filter, thus signal component 2234c during this period t2b to t2c corresponds to the amount of label dye bound to analyte bound to both the first and second micro bead 2105, 2106. During the time period from t2c to t2d, light emanating from the second micro bead 2106 is blocked by non-transmissive region 2126b-2 and the first micro bead is passing through transmissive region 2126a-2. During the period t2c to t2d the amplitude of signal component 2434c corresponds to the amount of label antibody bound to the first micro bead. During the time period t2d to t3, both first and second micro beads 2105, 2106 are within transmissive region 2126a-2 and signal component 2234c corresponds to the amount of label antibody bound to both micro beads 2105, 2106. During the period t3 to t4, light emanating from the first micro bead 2105 is blocked by non-transmissive region 2126b-3 and the second micro bead 2106 is within transmissive region 2126a-2. Thus, during time period t3 to t4, signal component 2234 corresponds to the label antibody bound to the second micro bead.

Note that the high frequency modulation in the signal 2234a is somewhat slower than the high frequency modulation in the signal 2234b, and the high frequency modulation in the signal 2234b is somewhat slower than the high frequency modulation in the signal 2234c because in this example, v1 is assumed to be less than v2 and v2 is assumed to be less than v3. Note also that the high frequency modulations in signals 2234a, 2234b, and 2234c are faster than the modulation associated with the spatial filter 2126. This is because v1, v2, and v3 are assumed in this case to be greater than the modulation associated with the spatial filter (and the speed of the micro beads).

Figure 23:
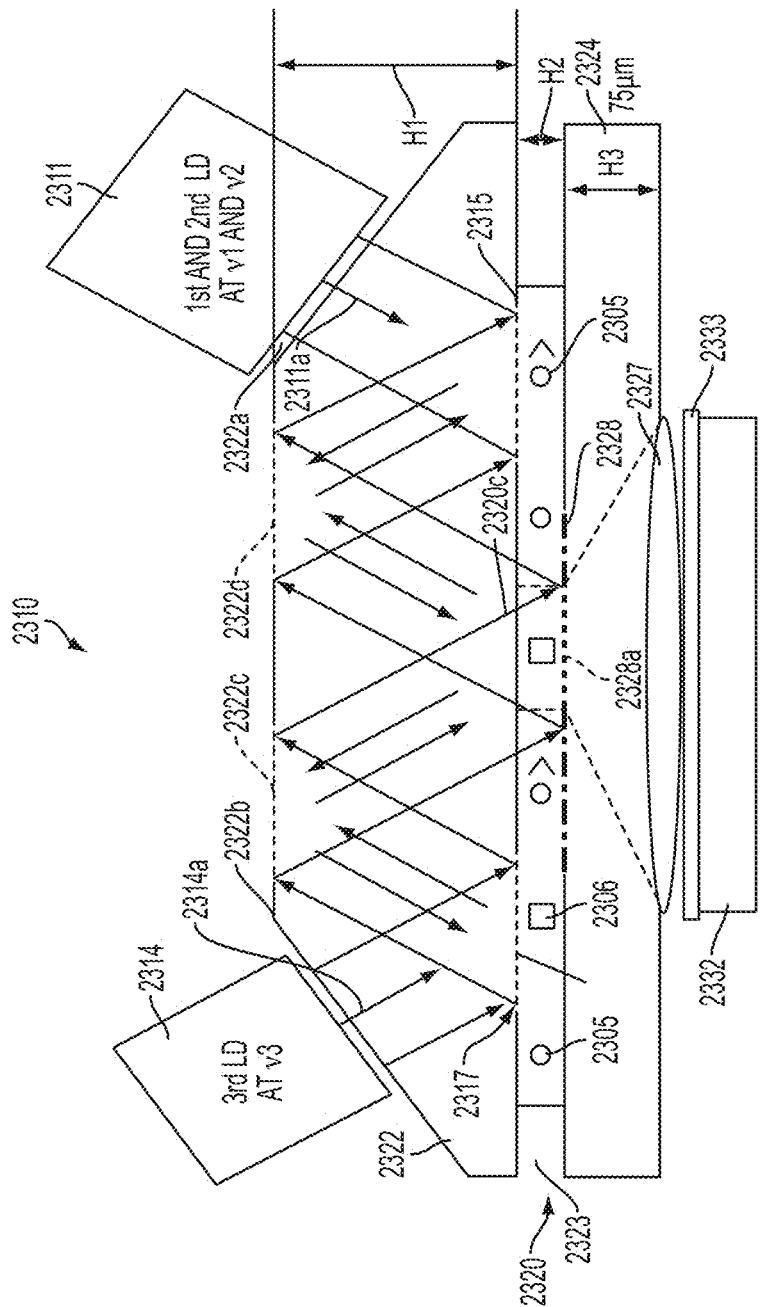
FIG. 23 is a schematic side or sectional view of another sample analyzer.

Another sample analyzer 2310 is shown schematically in FIG. 23. This analyzer, and the other analyzers described herein, may be or comprise a compact flow cytometer to perform multiplexed assays performed at the point of care (POC). Note that a slightly modified version of this POC testing device can be used in a broader sense for field testing of systems (e.g., integrity testing of a filtering system. The analyzer 2310 includes a fluidic device 2320 which may be a fluidic chip. The fluidic device 2320 is adapted to receive the sample of interest to be tested, and to cause the sample to flow through a flow channel 2323 formed between confining members 2322, 2324. A syringe, a peristaltic pump, or other suitable device may be used to provide such sample flow. The sample may include micro beads 2305 of a first type and micro beads 2306 of a second type which have been encoded by k dyes, e.g., first and second dyes having first and second excitation characteristics as discussed elsewhere herein. A label antibody used to detect one or more analytes in a sample has a third excitation characteristic. First and second excitation light produced by first and second light sources, respectively, may be combined, as described in conjunction with FIG. 24. Combined light source 2311, which provides combined first and second excitation light 2311a, is coupled to a first interface 2322a of the confining member 2322. A third light source 2314 generates third excitation light 2314a and is coupled to a second interface 2322b of the confining member 2322. The interfaces 2322a and 2322b are angled surfaces of the confining member 2322 to allow excitation light 2311a, 2314a from the light sources 2311, 2314 to propagate within the confining member 2322 and illuminate an excitation region 2320a of the flow channel 2323.

The combined light source 2311 emits combined excitation light 2311a that includes first excitation light and second excitation light. The first and second excitation light may be combined using collimating lenses and a beam splitter not shown in FIG. 23, but discussed and shown in FIG. 24. First excitation light is centered at or peaks at a first wavelength λ1, and second light is centered at or peaks at a second wavelength λ2. A third light source 2314 may emit third excitation light 2314a that is centered at or peaks at a third wavelength λ3. The confining member 2322 is substantially transmissive to wavelengths λ1, λ2, and λ3. The first, second, and third light sources are preferably solid-state devices such as laser diodes or LEDs.

In the depicted embodiment, combined light 2311a is internally reflected by a first lower mirror 2315 and then internally reflects against a first upper inner surface 2322d of confining member 2322 as shown in the figure before illuminating the excitation region 2320a of the flow channel. Light 2314a is similarly internally reflected by a second lower mirror 2317 and then internally reflects against the second upper inner surface portion 2322c of confining member 2322 before illuminating substantially the same excitation region 2320a. In some cases, one or more of mirrors 2317, 2315 may be omitted and replaced with total internal reflection (TIR) at an air interface, e.g. by providing suitable air gaps (note that the flow channel 2323 can be redirected or reconfigured such that it does not reside in the vicinity of mirrors 2317, 2315).

The first excitation light which is a first component of combined excitation light 2311a is effective to excite light emission from the first dye (while not substantially exciting light emission from the second or third dyes); the second excitation light which is a second component of combined excitation light 2311a is effective to excite light emission from the second dye (while not substantially exciting light emission from the first or third dyes); and the third excitation light 2314a is effective to excite light emission from the third (label) dye (while not substantially exciting light emission from the first or second dyes that encode the micro beads).

Preferably, the first excitation light is modulated at a first frequency v1, and the second excitation light is modulated at a second frequency v2, and the third excitation light is modulated at a third frequency v3, where v1, v2, and v3 are distinguishable from each other, such that the light emanating from the first encoder dye fluctuates at frequency v1, light emanating from the second encoder dye fluctuates as frequency v2 and the light emanating from the label dye fluctuates at frequency v3.

Light emanating from the various micro beads 2305, 2306 is detected by photosensitive detector 2332. Detector 2332 may have an associated spatial filter 2328 in order to derive more information from the excited micro beads. As illustrated in FIG. 23, the spatial filter 2328 can be disposed on the fluidic device 2320 or may be disposed in the path of light emitted by one or more of the light sources 2314, 2311 and/or may be remotely imaged onto the flow channel. A working portion 2328a of the filter 2328, characterized by a sequence of transmissive and non-transmissive regions arranged along the longitudinal direction. Light that travels through the spatial filter is optionally imaged by an optional optical element 2327 such as one or more suitable lenses and/or mirrors onto the detector 2332. The optical element 2327 may provide magnification, in which case the detector area that receives light that traverses through the spatial filter 2328 may be larger than the working portion 2328a of the spatial filter.

The detector 2332 provides a detector output which varies in time in accordance with at least: the passage of excited micro beads through the detection portion(s) of the flow channel 2323; the pattern of transmissive and non-transmissive regions of the spatial filter 2328; and the modulation of the excitation light sources. The detector output may be evaluated and analyzed using the various signal analysis techniques discussed herein. An optical emission filter 2333 may be provided for detector 2332 in order to block at least any residual excitation light that would otherwise fall on the detector 2332, while transmitting at least some of the light emission from the first, second, and third dyes.

In an exemplary embodiment, the analyzer 2310 may be made in a relatively small format suitable for use in POC applications. In such embodiment, the dimensions H1, H2, and H3 in FIG. 23 may be as follows: H1 may be about 500 μm to about 2 mm; H2 may be about 25 μm; and H3 may be about 75 to about 100 but these dimensions should not be construed to be limiting.

Figure 24:
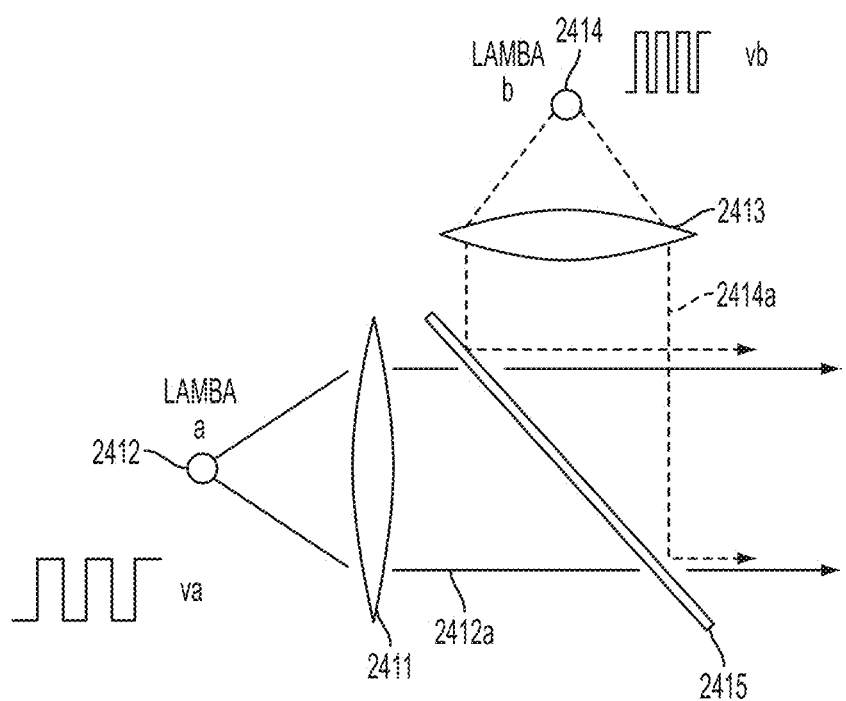
FIG. 24 is a schematic diagram of an arrangement for combining excitation light beams from two light sources.

FIG. 24 is a schematic diagram of one arrangement, out of many possible arrangements, for combining excitation light beams so that each of the light beams can illuminate a designated excitation region of a flow channel. In the implementation illustrated in FIG. 24, two independently modulated light sources are combined, however, the technique can be used to combine the modulated outputs from more than two light sources. As illustrated in FIG. 24, light sources 2412, 2414 have small emitting surfaces and emit excitation light over a range of angles. This excitation light is at least partially collimated by suitable optical elements such as lenses 2411, 2413, respectively, to produce collimated light beams 2412a, 2414a as shown. The sources are preferably LEDs or laser diodes capable of direct modulation via a modulated drive current, but any suitable sources of excitation light and modulation techniques may be used. The source 2412 emits light in a relatively narrow spectral band centered at wavelength λ1 and is modulated at a frequency ν1. The source 2414 emits light in a relatively narrow spectral band centered at wavelength and is modulated at a frequency ν2. A beam splitter 2415 transmits at least some of the light beam 2412a and reflects at least some of the light beam 2414a such that the resultant beams can be made to substantially overlap with each other, so that they can provide substantially overlapping excitation regions in a flow channel of an analyzer. The flow channel is not shown in FIG. 24 but may be provided at the right side thereof. Note that there are many other techniques for combining the output of light sources. Combining light sources may be accomplished, for example, via fiber coupling. Alternatively, multiple light sources could be mounted out of the plane of FIG. 23, for example, targeting the same detection area around the fluidic chip, and providing a ring space for many light sources.

Figure 25:
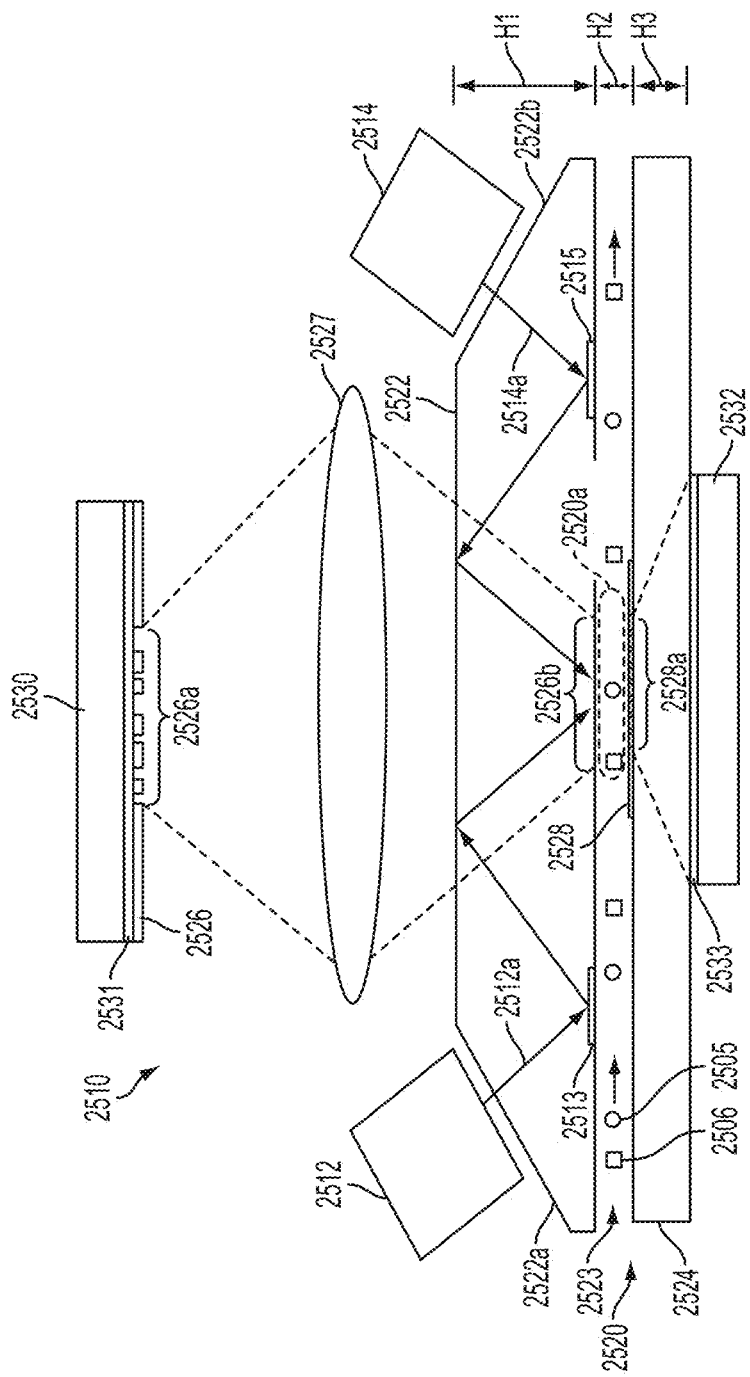
FIG. 25 is a schematic side or sectional view of another sample analyzer.

Another sample analyzer 2510 is shown schematically in FIG. 25. This analyzer may be or comprise a POC flow cytometer. The analyzer 2510 includes a fluidic device 2520 which may be a fluidic chip. The fluidic device is adapted to receive the sample of interest to be tested, and to cause the sample to flow through a flow channel 2523 formed between confining members 2522, 2524. A syringe, peristaltic pump, or other suitable device may be used to provide such sample flow. The sample may include micro beads 2505 of a first type and micro beads 2506 of a second type having dyes in different proportional relationships as discussed elsewhere herein. A combined light source 2512 provides a combined excitation light 2512a from first and second light sources. A third light source 2514 outputs third excitation light 2514a. The combined light source 2512 and the third light source 2514 are coupled to respective interfaces 2522a, 2522b of the confining member 2522, the interfaces being angled surfaces of the confining member 2522 to allow excitation light from the light sources to propagate within the confining member 2522 and illuminate an excitation region 2520a of the flow channel 2523. The first light source may emit first excitation light that is centered at or peaks at a first wavelength λ1 and the second light source may emit second excitation light that is centered at or peaks at a second wavelength λ2, wherein combined excitation light 2512a includes light of both wavelengths λ1 and λ2. The third light source 2514 emits third excitation light having wavelength λ3. The confining member 2522 is substantially transmissive to wavelengths λ1, λ2, and λ3. The first, second, and third light sources are preferably solid state devices such as laser diodes or LEDs. In the depicted embodiment, light 2512a is internally reflected by a first mirror 2513 and then internally reflects against an inner boundary surface of confining member 2522 as shown in the figure before illuminating the excitation region 2520a of the flow channel. Light 2514a is similarly internally reflected by a second mirror 2515 and then internally reflects against the inner boundary surface of confining member 2522 before illuminating substantially the same excitation region 2520a. In some cases, one or both of mirrors 2513, 2515 may be omitted and replaced with total internal reflection (TIR) at an air interface, e.g. by providing suitable air gaps (note that the flow channel 2523 can be redirected or reconfigured such that it does not reside in the vicinity of mirrors 2513, 2515).

The combined excitation light 2512a includes first excitation light which is effective to excite light emission from the first encoder dye (while not substantially exciting light emission from the second encoder dye or from the label dye); the combined excitation light 2512a also includes second excitation light which is effective to excite light emission from the second encoder dye (while not substantially exciting light emission from the first encoder dye or from the label dye). The third excitation light 2514a is effective to excite light emission from the label dye but not from the first or second encoder dyes. Preferably, the first excitation light is modulated at a first frequency ν1, and the second excitation light is modulated at a second frequency ν2 different from ν1, and the third excitation is modulated at a third frequency ν3 which is different from ν1 and ν2.

Light emanating from the various micro beads is detected by photosensitive detectors 2530, 2532. Each of these detectors may have its own spatial filter associated with it in order to derive more information from the micro beads. A first spatial filter 2526 is disposed at the detector 2530. A working portion 2526a of the filter 2526, characterized by a sequence of transmissive and non-transmissive regions arranged along the longitudinal direction, is imaged by an optical element 2527 such as one or more suitable lenses and/or mirrors onto a detection portion 2526b of the flow channel 2523. The optical element 2527 may provide magnification, in which case the detection portion 2526b may be smaller or larger than the working portion 2526a. In this configuration, the detector 2530 and the spatial filter 2526 are both remotely disposed relative to the fluidic device 2520. The remote configuration can allow for more convenient repair or replacement of the remotely-located parts, e.g., the detector 2530 and/or the spatial filter 2526. In some cases, for example, the spatial filter 2526 may be removeably mounted to allow for replacement with a different spatial filter having a different pattern of transmissive and non-transmissive regions. The remote detector channel can be suitable for sensing light emission from the encoder dyes (e.g., dye 1 and 2) because the light emission from the encoder dyes is relatively strong.

By contrast detector 2532, and its associated spatial filter 2528, are not remotely located but are instead disposed locally, i.e., at or on the fluidic device 2520. This local configuration can allow for a more compact and simpler design than a remote configuration and can provide for a higher SNR for weaker signals, e.g., from label dyes. The spatial filter 2528 has a working portion 2528a, which is disposed at or on the confining member 2524 at an edge or boundary of the flow channel 2523. The working portion 2528a also corresponds to a detection portion of the flow channel 2523 for purposes of detector 2532. The portion 2526b and the portion 2528a may be of the same or nominally the same size, and both may substantially overlap with the excitation region 2520a.

Each of the detectors 2530, 2532 provides its own detector output which varies in time in accordance with at least: the passage of excited micro beads through the detection portion(s) of the flow channel 2523; the pattern of transmissive and non-transmissive regions of the respective spatial filter; and the modulation of the excitation light sources. Each of these detector outputs may then be evaluated and analyzed independently of each other in separate signal processing channels using the various signal analysis techniques discussed herein. Optical emission filters 2531, 2533 may be provided for the respective detectors 2530, 2532 in order to block at least any residual excitation light that would otherwise fall on the detectors, while transmitting light emanating from at least one of the dyes. In some cases, the filters 2531, 2533 may each transmit emanating light from both the first and second encoder dyes as well as the label dye, such that the outputs of each detector 2530, 2532 contain signal contributions from the first and second dyes as well as the label dye. In other cases, at least one of the filters 2531, 2533 may block not only the first, second, or third excitation light but also light that emanates from one of the encoder dyes and/or the label dye. For example, filter 2531 may block light emanating from the label dye but may transmit light emanating from the first and second dyes. Filter 2533 may block light emanating from the first and second dyes but may transmit light emanating from the label dye. In general, a local filter and detector may be used to detect a smaller signal, e.g., the third light emission emanating from the label dye. A remote filter and detector may be suitable to detect the first and second light emission emanating from the first and second encoder dyes, because the first and second light emission components from the first and second encoder dyes are much larger than the third light emission from the label dye.

Furthermore, a variety of configurations for the detectors and the spatial filters are also contemplated. For example, analyzer 2510 may be modified to provide: a remote detector 2532 but a local spatial filter 2528; a remote detector 2532 and a remote spatial filter 2528; a remote detector 2530 but a local spatial filter 2526; and a local detector 2530 and a local spatial filter 2526. In some cases, the spatial filter 2526 may have substantially the same arrangement or pattern of transmissive and non-transmissive regions as spatial filter 2528. In other cases, the patterns for these filters may be different. One spatial filter may have a periodic pattern, while the other spatial filter may have a non-periodic pattern. Alternatively, one spatial filter may have a first periodic pattern, and the other spatial filter may have a second periodic pattern different from the first pattern. Alternatively, one spatial filter may have a first non-periodic pattern, and the other spatial filter may have a second non-periodic pattern different from the first pattern. One spatial filter may have a monochromatic pattern, while the other spatial filter may have a polychromatic pattern. Alternatively, both spatial filters may have monochromatic patterns, or both may have polychromatic patterns. Furthermore, the detectors 2530, 2532 may have substantially the same detector characteristics, or they may be different. For example, the detectors 2530, 2532 may both be silicon photodiodes, or they may be photodiodes made of some other detector material, and they may thus have substantially the same spectral responsivity. Alternatively, the detectors 2530, 2532 may be composed of different detector materials (e.g., different semiconductors), and they may thus have substantially different spectral responsivities.

In an exemplary embodiment, the analyzer 2510 may be made in a relatively small format suitable for use in POC applications. In such embodiment, the dimensions H1, H2, and H3 in FIG. 16 may be similar to those of FIG. 23.

The concept shown in FIG. 25 of using two different detector/spatial filter combinations can be extended in a straightforward fashion to more than two such combinations. For example, three, four, or more different detectors and/or detector/spatial filter combinations may be used for a given flow channel and analyzer. Furthermore, two, three, or more modulated laser diodes or other modulated excitation sources may be arranged to illuminate substantially the same excitation region 2520a, for example, by arranging such sources in a ring geometry. Such concepts can also be applied to the other analyzers disclosed herein. The analyzer of FIG. 25 enables the use of separate detectors for identifying the micro bead types (denoted the identifier channel) and for detecting the presence of analyte (denoted the reporter channel). In this configuration, the third light source used to excite the label dye does not necessarily have to be modulated. In such a configuration, it may be beneficial to not modulate the light source used to excite the label dye since the non-modulated signal can allow better SNR discrimination if the spatial modulation technique is used. Furthermore, information needed for more sophisticated data evaluation e.g., triggering on micro bead detection and/or use of the micro bead speed and/or use of the shape of the signal for analysis can be accomplished using the much stronger signal from the first and second dyes from the identifier channel.

Note that, optionally, a lens may be disposed between the flow channel and the detector. Using a lens in this location can allow for better filtering of the excitation light and separation of the excitation light from the light emitted from the dyes. For example, the previously mentioned notch filters may be dielectric stacks that optimally need parallel light path. Direct sensing without an imaging lens may be more appropriate for use with lower quality color filters. On the other hand, direct sensing allows for very high light collection. Note that an imaging lens could be formed as an integral part of the confinement layer 2524, e.g., produced by injection molding. In the case of direct sensing, the confinement layer 2524 itself can represent the color filter if a suitable material is chosen. In general, using color filters provides only limited suppression of the excitation lights and is prone to native fluorescence stimulated by the excitation sources. Such native fluorescence would also be modulated with the same frequency of the excitation sources.

Figure 26:
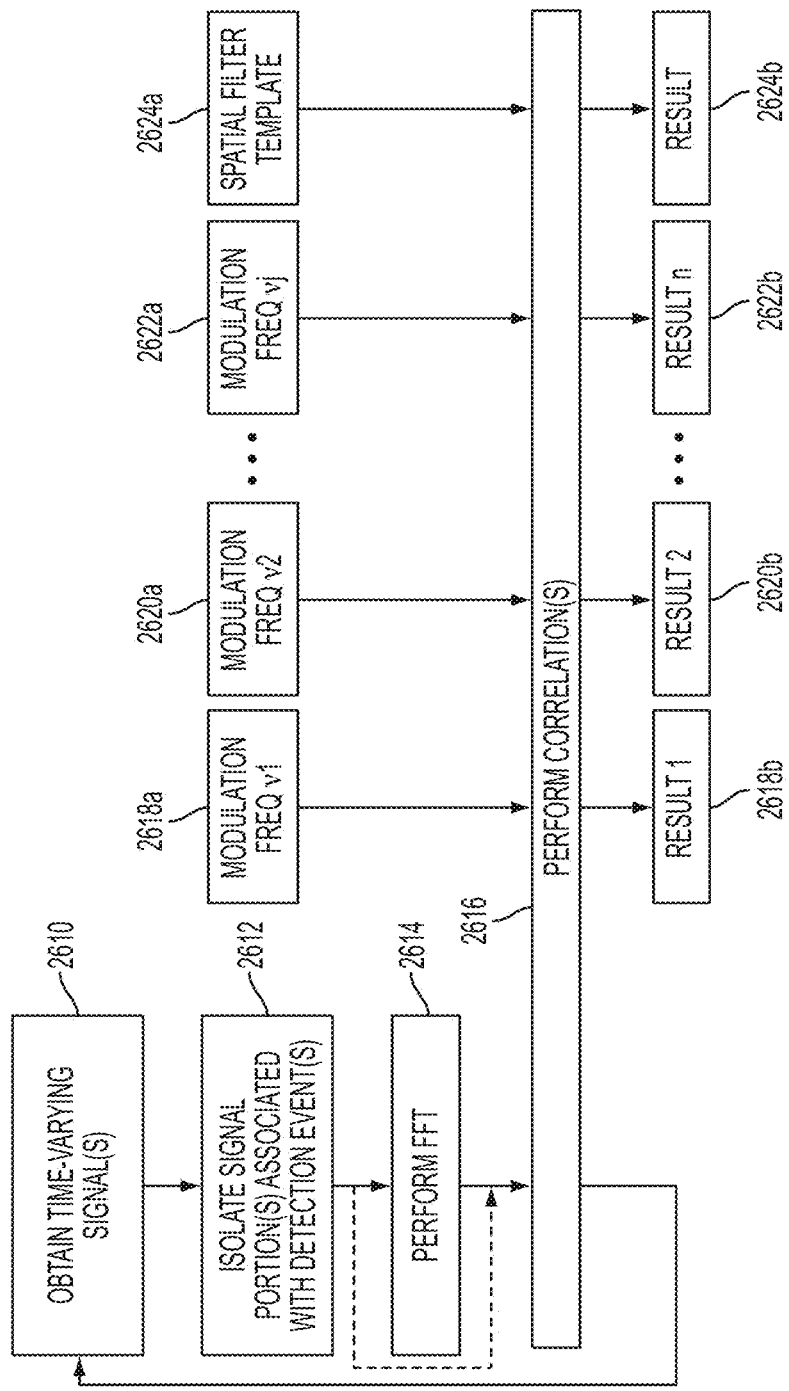
FIG. 26 is a flow diagram depicting various processes that can be carried out with the disclosed sample analyzers.

FIG. 26, shows a flow diagram of processes that may be used in at least some implementations of the disclosed sample analyzers. In box 2610, time-varying signal(s) are obtained from the photosensitive detector(s). (More than one detector may be used on a given analyzer, and each detector may have its own spatial filter, as discussed above.) In box 2612, portions of each time-varying signal associated with detection events are isolated. This procedure can be used when there is a large quantity of micro beads and/or may also be used when dealing with rare event detection. In rare event detection, the detector output may be substantially zero (e.g., at or near the noise floor) for significant periods of time, interrupted by sporadic signal bursts corresponding to a micro bead of interest passing through the detection portion of the flow channel. In either case, passage of one or more micro beads through the detection portion of the flow channel is referred to as a detection event. The portion of the time-varying signal corresponding to such a sporadic signal burst may be separated and isolated for individual evaluation and analysis. Note that, even in cases involving high micro bead concentrations, where at least one micro bead is likely to be present in the detection portion of the flow channel at any given time, the continuous time-varying output signal of the detector may be subdivided into isolated signal portions of manageable size for signal processing purposes. The isolated signal portion may also represent a sliding time window of the continuous detector output, e.g., being constantly updated with the newest raw data points as the oldest raw data points are discarded.

In box 2614, a frequency spectrum of each signal portion is calculated. The frequency spectrum may be calculated using a fast Fourier transform (FFT) technique, or by any other suitable technique. In addition to calculation of the frequency spectrum, some analysis may be carried out. Local maxima or peaks, and/or a dominant peak, in the frequency spectrum may be identified, and their coordinates in amplitude and frequency may be measured and stored. The amplitude of the frequency spectrum may be measured at one or more predetermined frequencies, such as at the modulation frequencies ν1, ν2 of the light sources. The measured amplitudes may be compared to each other and/or to one or more threshold values, e.g., so as to distinguish from the noise floor or to distinguish small signal levels from large signal levels. Ratios of the amplitudes may also be calculated. Information about the magnitudes of the signal at frequencies used to excite the encoder dyes may be used to identify the micro bead types.

In box 2616, correlations may be performed on the signal portion of the detector output. For example, correlations between the signal portion and the modulation frequencies, shown in boxes 2618a, 2620a, ..., 2622a, may be calculated, with the results shown respectively in boxes 2618b, 2620b, ..., 2622b. Furthermore, the correlation between the signal portion and a template signal, shown in box 2624a, may be calculated to provide a result shown in box 2624b. The template signal may be representative of the spatial transmission function of the spatial filter. If the spatial transmission function (and hence also the template signal) is non-periodic, this correlation of the signal portion with the template signal can be used to determine the longitudinal position of the micro bead in the flow channel.

In some cases, correlations in box 2616 involving the modulation frequencies ν1, ν2, . . . νj can be performed without calculating an entire frequency spectrum as in box 2614. In other cases, calculation of the frequency spectrum in box 2614 may be performed without calculating the correlations in box 2616.

Figure 27:
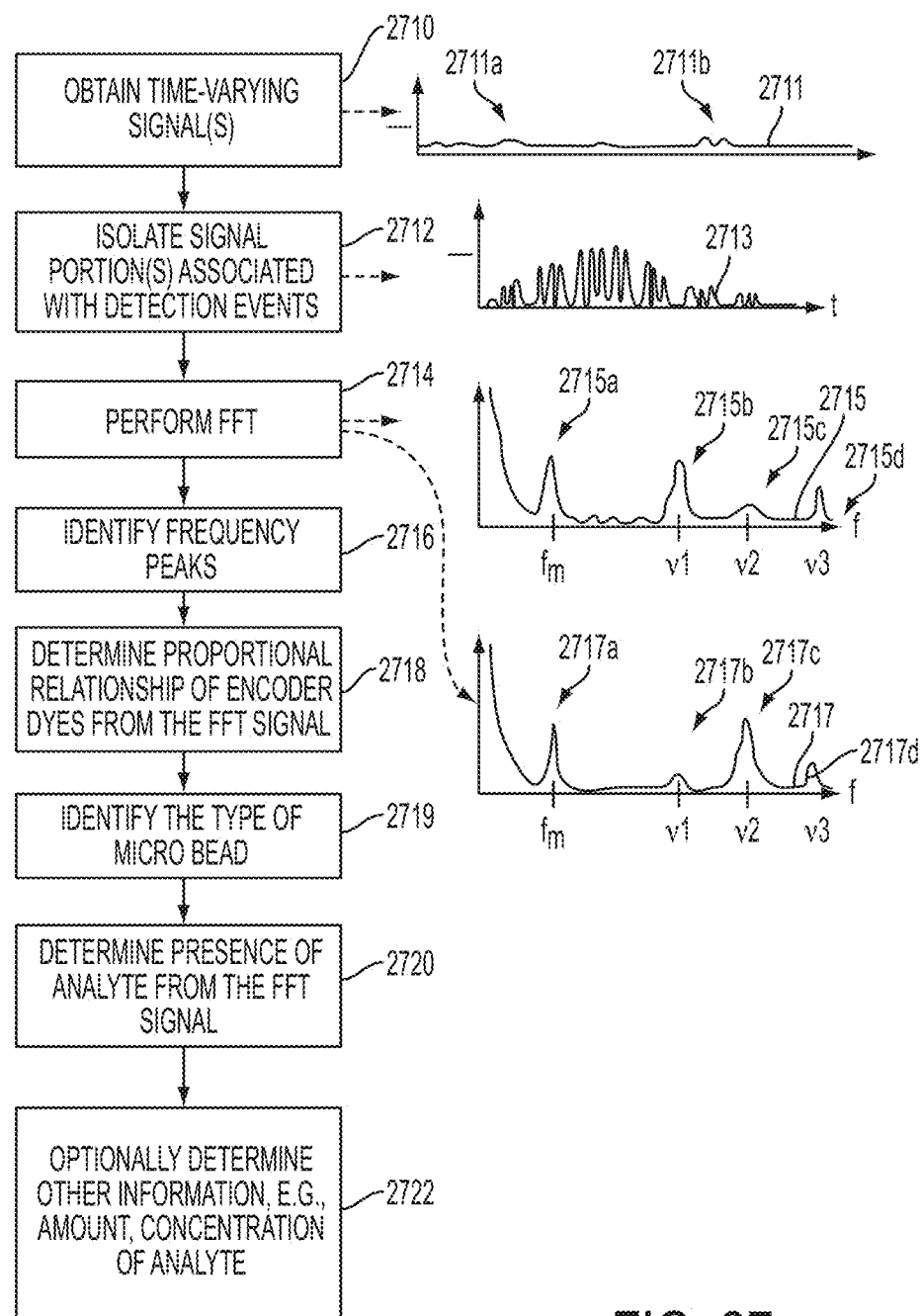
FIG. 27 is a flow diagram depicting various processes that can be carried out with the disclosed sample analyzers.

FIG. 27 shows a flow diagram including various processes that may be used in at least some implementations of the disclosed sample analyzers. Processes shown in the boxes of FIG. 27 and other flow diagrams described herein may be implemented by hardware, software, firmware, or a combination of hardware, software and/or firmware. The processes shown in FIG. 27 may be implemented, for example, by the processors 1240, 1940, 2040, (FIGS. 12, 19, and 20) by carrying out a series of program steps. In box 2710, time-varying signal(s) are obtained from the photosensitive detector(s). A possible detector output signal 2711 is shown in a graph of intensity (I) versus time (t), the signal having signal bursts 2711a, 2711b indicative of the presence of a micro bead in the detection channel. In box 2712, portions of each time-varying signal associated with detection events are isolated. A possible signal portion 2713 associated with one such detection event is shown in a graph of intensity (I) versus time (t).

In box 2714, a frequency spectrum of each signal portion is calculated, e.g., using a fast Fourier transform (FFT) technique or other suitable technique. Two possible outcomes of this procedure are shown as frequency spectrum 2715 and frequency spectrum 2717, each spectrum plotted on a graph of amplitude (magnitude) versus frequency (f). The spectrum 2715 is representative of a signal portion containing information from a first type of micro bead, which is excited by the first light source at the modulation frequency ν1 at a first (larger) magnitude and is excited by the second light source at the modulation frequency ν2 at a second (smaller) magnitude according to the proportional relationship of first and second encoder dyes characteristic for the first type of micro bead. The spectrum 2715 contains a major frequency component 2715b at the frequency ν1 associated with the first encoder dye, a major frequency component 2715c at ν2 associated with the second encoder dye, a major frequency component 2715a at the mask frequency $f_m$, and a major frequency component 2715d at ν3 associated with the label dye. (The peaks at the mask frequency $f_m$ assume the spatial filter has a transmission function that is periodic or substantially periodic. The frequency $f_m$ corresponds to the spatial frequency of the spatial filter multiplied by the speed of the micro bead.)

The spectrum 2717 is representative of a signal portion containing information from the second type of micro bead, which is excited by the first light source at the modulation frequency ν1 at a first (smaller) magnitude and is excited by the second light source at the modulation frequency ν2 at a second (larger) magnitude according to the proportional relationship of first and second encoder dyes characteristic of the second type of micro bead. The spectrum 2717 contains a major frequency component 2717b at the frequency ν1 at a first (smaller) magnitude which is associated with the first encoder dye, a major frequency component 2717c at the frequency ν2 at a second (larger) magnitude which is associated with the second encoder dye, a major frequency component 2717a at the mask frequency $f_m$, and a major frequency component 2717d at ν3 which is associated with the label dye.

In box 2716, additional analysis may be carried out. Local maxima or peaks, and/or a dominant peak, in the frequency spectrum may be identified, and their coordinates in amplitude and frequency may (be measured and stored. The amplitude of the frequency spectrum may be measured at one or more predetermined frequencies, such as at the modulation frequencies ν1, ν2, ν3 of the light sources. These amplitudes may be compared with each other and/or with other thresholds or parameters. Ratios of the amplitudes may also be calculated.

In box 2718 the proportional relationship of the encoder dyes is determined from the FFT signal. In box 2719, the type of micro bead is assessed by analyzing the components of FFT at the modulation frequencies of the first and second light sources. The proportional relationship of components at ν1 and ν2 is determined. Note that to simplify the explanation, proportional relationships of a two dye combination are used to characterize the different micro bead types, however, it will be appreciated that more than two dyes may be employed to encode the micro beads. Analysis of the proportional relationship of the at ν1 and ν2 components in the output signal is used to identify the micro bead type.

The component of the frequency spectrum associated with the label dye is analyzed 2720 and correlated to the type of the micro bead. The presence, amount and/or concentration of one or more analytes in the sample is determined 2720 based on the micro bead type and the indication provided by the label dye. For example, for the exemplary output spectrum 2715, the proportional relationship between the magnitudes of peak 2715b and peak 2715c indicates the presence of the first type of micro bead. The magnitude of the peak 2715d indicates the presence of the analyte recognized by the first type of micro bead. With reference to the exemplary output spectrum 2717, the proportional relationship between the magnitudes of peak 2717b and peak 2717c indicates the presence of the second type of micro bead. The magnitude of the peak 2717d indicates the presence of the analyte recognized by the second type of micro bead. Thus, the type of analytes present can be detected by the micro bead type and the indication of presence provided by the label dye. In addition, more sophisticated analysis can be performed 2722, such as determination of the amount or concentration of analyte in the sample.

Note that the signals corresponding to amounts of encoder dyes used to identify the type of micro bead are quite strong and can be used to extract features of the micro bead, such as speed of the micro bead, shape of signal, and/or exact position of particle which then helps to precisely determine even a very weak signal from the label dye which is needed to determine the presence/amount of analyte.

For example, besides signal amplitude for the various signal components, the speed of a given micro bead can also be computed based on a measurement of the mask frequency $f_m$ discussed above. This information can be combined with signal amplitude characteristics to provide further insight regarding micro bead characteristics of the sample. Note that the speed information of each micro bead can also be used to modify the frequency spectrum (e.g. FFT) and/or correlation signals by making adjustments according to micro bead speed. Since slower micro beads reside in the detection area for longer times than faster micro beads, the slower micro beads tend to provide larger fluorescence signals and higher correlation values than faster micro beads. The signal processing unit of the measurement system may implement appropriate normalization or other adjustment of the frequency spectrum and/or correlation signals to correct for this effect.

The FFT signal or other frequency component of the detector output signal at the source modulation frequencies v1 and/or v2 can be used as a micro bead trigger. Since the source modulation frequencies v1, v2 are known, and can be provided as inputs to the signal processing unit, this allows for the use of advanced electronic filtering (such as lock-in techniques and/or digital filtering) to provide extremely sensitive detection of micro beads and/or the analytes.

Fast Fourier transform analysis and/or correlation techniques can be used to provide detailed information about the micro beads and/or analyte, for example: details in the power (frequency) spectrum or in the value of the measured mask frequency $f_m$ (in the case of a periodic or substantially periodic mask) may be used to determine micro bead speed; correlations with different specific test/template functions can be used to provide detailed color information, lifetime of a fluorescence label, and so forth.

Figure 28:
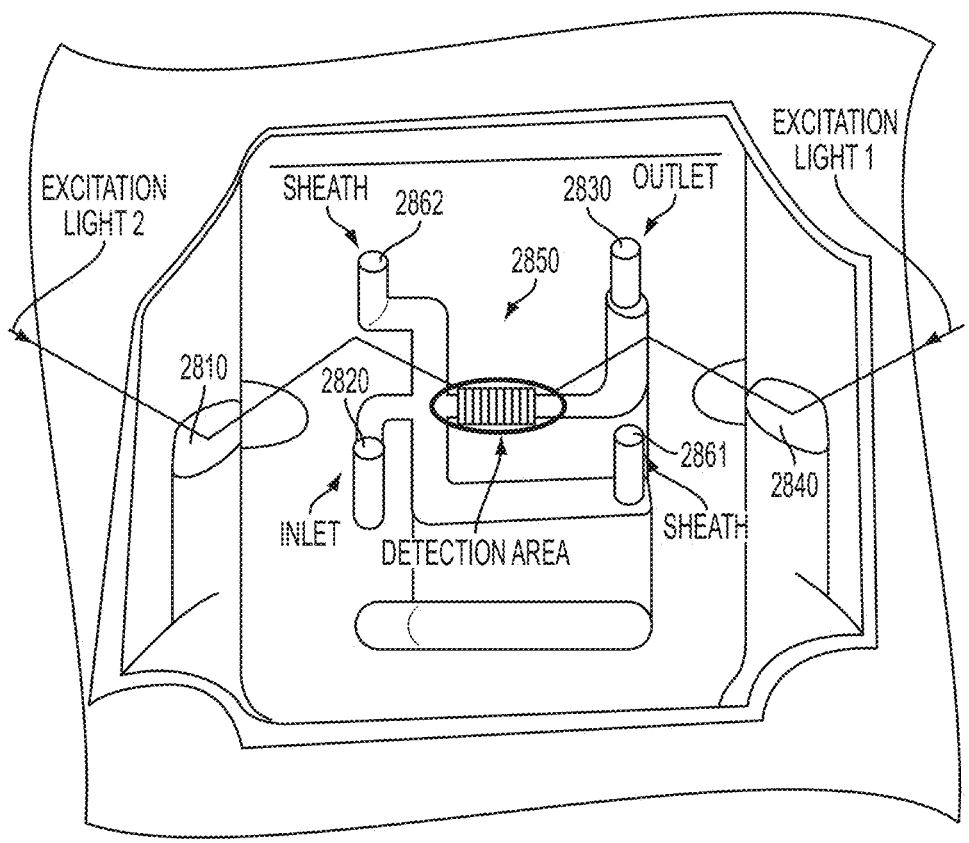
FIG. 28 is a photograph of the analyzer depicted schematically in FIG. 23.

FIG. 28 is a photograph of the analyzer depicted schematically in FIG. 23. The photograph shows the detection area 2850, a first optical interface 2840 for the first (e.g., combined) excitation light and a second optical interface 2810 for the second excitation light. Inlet 2820 allows entry of the sample into the analyzer and outlet 2830 allows the sample to exit the analyzer. The analyzer includes ports 2861 and 2862 that allow entry and/or exit of a sheath liquid. The use of sheath liquid for analyte focusing is optional and can be used for samples with high bead concentrations to reduce the likelihood of having multiple beads in the detection area at a time, for example.

Figure 29:
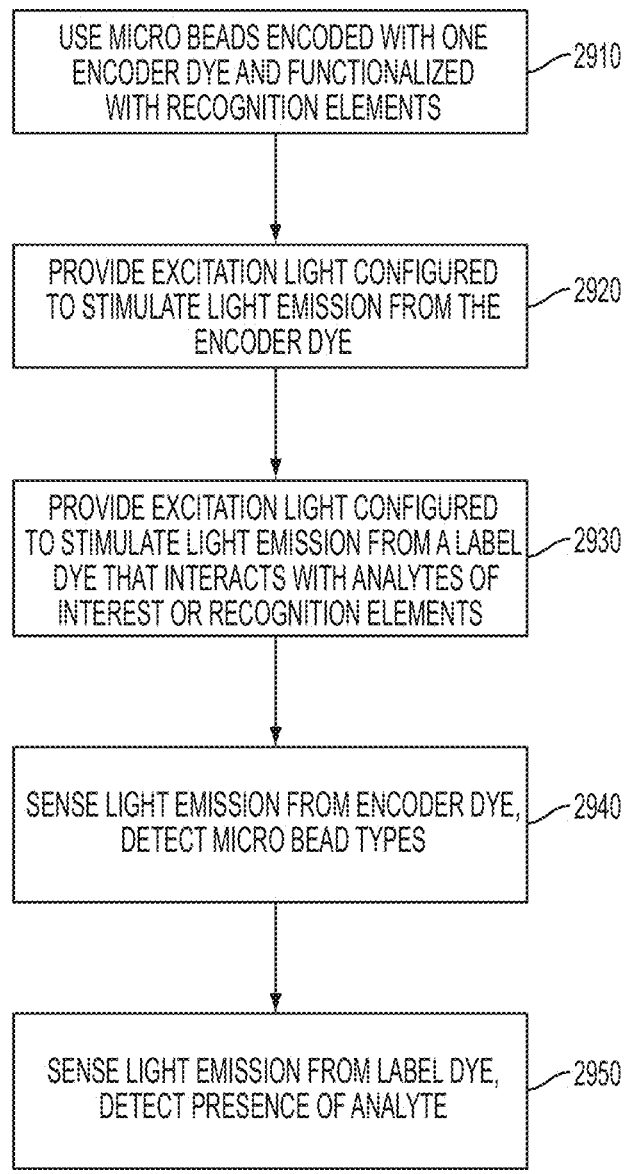
FIG. 29 is a flow diagram of a method of using one encoder dye to encode the micro beads which are functionalized with recognition elements.

In some implementations, as illustrated by the flow diagram of FIG. 29, a simplified analysis approach involves using 2910 only one encoder dye to encode the micro bead types. The micro beads are functionalized with recognition elements. A label dye is used to detect the analyte by interacting with the analyte, the recognition elements and/or according to any of the various processes for analyte detection previously discussed. This approach can be carried out using an analyzer that includes two light sources, such as the analyzer depicted in FIG. 12. The first light source provides 2920 first excitation light modulated at frequency v1 used to excite the encoder dye. The second light source provides 2930 second excitation light v2 used to excite the label dye. Note that the modulation frequencies can range from Hz to MHz or may be 0 Hz. The light emission from the encoder dye is sensed 2940 and is used to detect the micro bead type. The light emission from the label dye is sensed 2950 and is used to detect the analyte.

Figure 30:
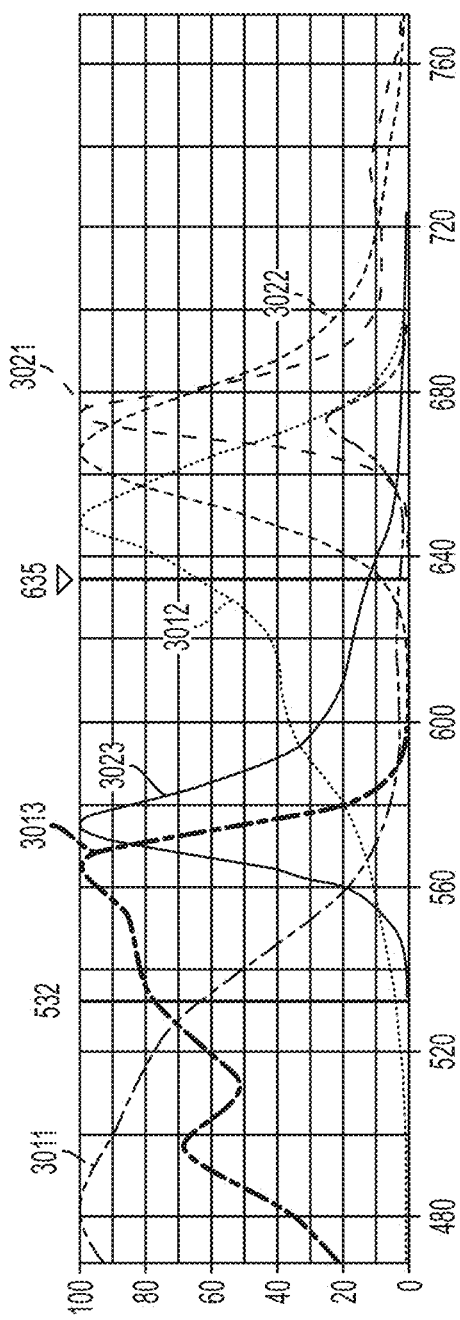
FIG. 30 provides sets of graphs showing absorption and emission spectra for illustrative fluorescent dye combinations that may be used to encode micro beads in proportional relationships so as to indicate different micro bead types wherein one light source is used to excite light emission from two dyes.

In some cases, one light source may be used to excite two dyes. In these implementations, it is helpful if the two dyes stimulated by the same light source, and thus intensity modulated by the same frequency, have different emission spectra that can be separated during the detection portion of the process using optical filtering. FIG. 30 shows absorption 3011, 3012 and emission spectra 3021, 3022 of PerCP and APC dyes, respectively, used in conjunction with R-phycoerthrin (R-PE), having absorption 3013 and emission spectra 3023. The PerCP/APC/R-PE combination is one possible dye combination for this technique.

The analyzer that would be used for an approach that uses one light source to excite two dyes may be similar to the analyzer shown in FIG. 25 that employs two detector channels. However, in this implementation, light source 2512, which was previously described as a combined light source, emitting a combined light 2512a having two excitation wavelength ranges, need only emit a single wavelength range. In this implementation, the PerCP and R-PE dyes can be excited using a first light source 2512 emitting excitation light having a wavelength range centered at about 532 nm. The APC dye is excited using a second light source 2514 emitting excitation light 2514a having a wavelength range centered at about 635 nm.

Detector 2530 can be used to detect light emission from both the PerCP and APC dyes, and the light emission from these dyes can be distinguished because they are modulated at different frequencies. Optical filter 2531 would be configured to substantially block wavelengths emitted by the R-PE dye to prevent cross-talk between the light emission from the PerCP and R-PE dyes. Optical filter 2531 can also be configured to substantially block the wavelengths of the excitation light (at 532 nm and 635 nm). Analysis of the detector signal generated by detector 2530 will reveal the micro bead type.

Detector 2532 can be used to detect light emission from the R-PE dye. Optical filter 2533 can be used to block light emission from the APC and PerCP dyes and the excitation light from sources 2512, 2514. Analysis of the detector signal generated by detector 2532 will be indicative of the presence (or absence) of the analyte.

Unless otherwise indicated, all numbers expressing feature sizes, amounts, physical properties, and so forth used in the specification and claims are to be understood as being modified by the term "about". Accordingly, unless indicated to the contrary, the numerical parameters set forth in the specification and claims are approximations that can vary depending on the desired properties sought to be obtained by those skilled in the art utilizing the teachings of the present application.

It will be appreciated that variants of the above-disclosed invention, and other features and functions, or alternatives thereof, may be combined into many other different systems or applications. Various presently unforeseen or unanticipated alternatives, modifications, variations, or improvements therein may be subsequently made by those skilled in the art, and are intended to be encompassed by the following claims.

The invention claimed is:

1. A method, comprising:
stimulating light emission from k dyes encoding n type of absorption-encoded micro beads present in a sample, each k dye having an absorption spectrum that is distinguishable from absorption spectra of others of the k dyes, wherein stimulating the light emission comprises selectively stimulating each of the k dyes without substantially stimulating others of the k dyes, the k dyes encoding n types of absorption-encoded micro beads, each type of micro bead encoded with amounts of the k dyes in a proportional relationship that is different from proportional relationships of the k dyes of others of the n types of absorption-encoded micro beads;
detecting one or more types of absorption-encoded micro beads present in the sample based on light emission from the k dyes that encode the types of absorption-encoded micro beads; and
analyzing one or more properties of a system using information obtained from detecting the one or more types of absorption-encoded micro beads.

2. The method of claim 1, wherein detecting the one or more types of absorption-encoded micro beads comprises detecting multiple types of the absorption-encoded micro beads and differentiating between the multiple types.

3. The method of claim 2, further comprising counting the absorption-encoded micro beads of each micro bead type.

4. The method of claim 1, wherein the information includes at least one of shape, surface texture, charge, material, hydrophilism, hydrophobism, elasticity, and porosity of the one or more types of absorption-encoded micro beads present in the sample.

5. The method of claim 4, wherein:
the system comprises a filter; and
the one or more properties comprise filter integrity.

6. The method of claim 1, wherein:
the system is a biological system;
the sample is taken from the biological system; and
the n-types of absorption-encoded micro beads are added to the sample.

7. The method of claim 1, wherein:
the n types of micro beads are functionalized with n types of recognition elements, respectively, the n types of recognition elements configured to interact with n analytes, respectively; and
analyzing the one or more properties of the system comprises determining whether one or more of the n analytes are present in the sample.

8. The method of claim 7, wherein functionalizing the n-types of recognition elements comprises creating an association between the n types of recognition elements and at least one additional dye.

9. The method of claim 8, wherein the at least one additional dye comprises one or more of Cy 5 and RP-E.

10. The method of claim 8, wherein $2 \leq k \leq 3$ and $20 \leq n \leq 1000$.

11. The method of claim 1, wherein the k dyes comprise one or more of:
DiA and Pacific Orange;
Pacific Blue and SYTOX Blue;
PerCP and APC; and
chlorophyll a and chlorophyll b.

12. The method of claim 1, further comprising:
providing excitation light configured to stimulate light emission from a label dye, the light emission indicative of a presence of one or more analytes in the sample;
sensing for light emanating from the micro beads, the light emanating from each micro bead including one or more of light emission from the k dyes and light emission from the label dye; and
detecting one or more target analytes present in the sample based on the light emanating from the micro beads.

13. The method of claim 12, wherein the n types of absorption-encoded micro beads are functionalized with n recognition elements, respectively, and detecting the one or more target analytes present in the sample comprises identifying multiple target analytes present in the sample.

14. The method of claim 12, wherein the label dye comprises one or more of:
a fluorophore-conjugated antibody configured to bind to a target analyte causing an increase in the light emanating from the micro beads when the target analyte is present in the sample;
a fluorophore-conjugated antibody configured to bind to a competitor molecule that is displaced from a recognition element of the micro beads by a target analyte causing a decrease in the light emanating from the micro beads when the target analyte is present in the sample;
a fluorophore-conjugated competitor molecule which is displaced from a recognition element of the micro beads by a target analyte causing a decrease in the light emanating from the micro beads when the target analyte is present in the sample;
a fluorophore conjugated to a recognition element of the micro beads, wherein a quencher-conjugated competitor molecule is displaced from a fluorophore-conjugated recognition element of the micro bead by binding to a target analyte, causing an increase in the light emanating from the micro beads when the target analyte is present in the sample.

15. The method of claim 12, wherein:
providing an excitation light configured to stimulate light emission from the k dyes comprises providing k types of excitation light intensity modulated, respectively, at k frequencies, $v1, v2, \ldots vk$;
sensing for the light emanating from the micro beads comprises sensing for light emission modulated at the k frequencies; and
detecting the one or more types of absorption-encoded micro beads present in the sample comprises detecting based on the modulated light emission from the k dyes.

16. The method of claim 12, wherein:
providing the excitation light configured to stimulate light emission from the label dye comprises providing excitation light modulated at a frequency, $v$;
sensing for the light emanating from the micro beads comprises sensing for light emission modulated at frequency $v$; and detecting the one or more target analytes present in the sample comprises detecting based on the light emission modulated at the frequency ν.

17. The method of claim 12, wherein:

providing excitation light configured to stimulate light emission from the k dyes and providing excitation light configured to stimulate light emission from the label dye comprises providing excitation light modulated at a frequency, ν, for at least one k dye and the label dye; and sensing for the light emanating from the micro beads comprises separating light emission from the at least one k dye and light emission from the label dye using an optical filter.

18. The method of claim 12, wherein:

detecting the one or more types of absorption-encoded micro beads present in the sample comprises detecting the one or more types of absorption-encoded micro beads using a first detector channel; and detecting the one or more target analytes present in the sample comprises detecting the one or more analytes using a second detector channel.

19. The method of claim 18, wherein:

the absorption-encoded micro beads present in the sample flow through a flow channel;

the first detector channel comprises a first photosensitive detector configured to sense for the light emission from the k dyes; and the second detector channel comprises a second photosensitive detector configured to sense for the light emission from the label dye, wherein the first photosensitive detector is spaced apart from the flow channel by a first distance and the second photosensitive detector is spaced apart from the flow channel by a second distance, and the first distance is greater than the second distance.

* * * * *